(12) United States Patent
Harari et al.

(10) Patent No.: US 7,527,185 B2
(45) Date of Patent: May 5, 2009

(54) COMPRESSION ANASTOMOSIS RING ASSEMBLY AND APPLICATOR FOR USE THEREWITH

(75) Inventors: Boaz Harari, Tel Aviv (IL); Leonid Monassevitch, Givat Olga (IL); Michael Arad, Tel Aviv (IL); Doron Kopelman, Caesarea (IL); Amir Perle, Haifa (IL)

(73) Assignee: Niti Surgical Solutions Ltd., Netanya (IL)

( * ) Notice: Subject to any disclaimer, the term of this patent is extended or adjusted under 35 U.S.C. 154(b) by 320 days.

(21) Appl. No.: 11/485,604

(22) Filed: Jul. 12, 2006

(65) Prior Publication Data

US 2008/0015617 A1    Jan. 17, 2008

(51) Int. Cl.
*A61B 17/08* (2006.01)
(52) U.S. Cl. ............................ 227/179.1; 227/19
(58) Field of Classification Search ............ 227/19, 227/179.1, 181.1
See application file for complete search history.

(56) References Cited

U.S. PATENT DOCUMENTS

| | | | |
|---|---|---|---|
| 4,055,186 A | 10/1977 | Leveen | |
| 4,304,236 A * | 12/1981 | Conta et al. | 227/179.1 |
| 4,476,863 A | 10/1984 | Kanshin et al. | |
| 4,505,272 A | 3/1985 | Utyamshev et al. | |
| 4,567,891 A | 2/1986 | Kanshin et al. | |
| 4,752,024 A * | 6/1988 | Green et al. | 227/19 |
| 4,893,622 A * | 1/1990 | Green et al. | 227/180.1 |
| 4,957,499 A | 9/1990 | Lipatov et al. | |
| 5,171,252 A | 12/1992 | Friedland | |
| 5,197,648 A | 3/1993 | Gingold | |
| 5,271,543 A * | 12/1993 | Grant et al. | 227/179.1 |
| 5,312,024 A | 5/1994 | Grant et al. | |
| 5,344,059 A | 9/1994 | Green et al. | |
| 5,346,501 A | 9/1994 | Regula et al. | |

(Continued)

FOREIGN PATENT DOCUMENTS

EP    0 326 757 A1    8/1989

(Continued)

OTHER PUBLICATIONS

C. Wullstein and E. Gross, "Compression anastomosis (AKA-2) in colorectal surgery: results in 442 consecutive patients", British Journal of Surgery, 2000, vol. 87, pp. 1071-1075.

*Primary Examiner*—Brian D Nash
(74) *Attorney, Agent, or Firm*—Pearne & Gordon LLP

(57) ABSTRACT

A compression anastomosis ring (CAR) assembly for use in joining severed organ wall portions of a hollow organ. The assembly comprises a first portion which includes an anvil assembly and a second portion which comprises a bottom ring, at least one ring element, and at least one spring element formed of a shape-memory alloy. The at least one spring element provides a restorative force and is in compressive force contact with the bottom ring and the tissue to be joined is positioned between the anvil ring and the bottom ring. A plurality of needles on one of the ring elements is operative, upon application of a closure force, to pierce the tissue and the anvil ring, holding the anvil ring to the second portion of the CAR assembly. An applicator for applying the CAR assembly and a method for using the assembly and applicator are taught.

18 Claims, 20 Drawing Sheets

U.S. PATENT DOCUMENTS

| | | | |
|---|---|---|---|
| 5,411,508 A | 5/1995 | Bessler et al. | |
| 5,639,008 A | 6/1997 | Gallagher et al. | |
| 5,669,918 A * | 9/1997 | Balazs et al. | 606/139 |
| 5,758,814 A * | 6/1998 | Gallagher et al. | 623/23.72 |
| 5,951,576 A * | 9/1999 | Wakabayashi | 606/151 |
| 6,117,148 A | 9/2000 | Ravo et al. | |
| 6,171,321 B1 * | 1/2001 | Gifford et al. | 606/153 |
| 6,193,129 B1 * | 2/2001 | Bittner et al. | 227/180.1 |
| 6,402,765 B1 | 6/2002 | Monassevitch et al. | |
| 6,503,259 B2 * | 1/2003 | Huxel et al. | 606/153 |
| 6,884,250 B2 | 4/2005 | Monassevitch et al. | |
| 6,896,684 B2 | 5/2005 | Monassevitch et al. | |
| 6,899,718 B2 * | 5/2005 | Gifford et al. | 606/155 |
| 7,094,247 B2 * | 8/2006 | Monassevitch et al. | 606/153 |
| 2001/0001825 A1 * | 5/2001 | Snow et al. | 606/151 |
| 2002/0058955 A1 * | 5/2002 | Blatter et al. | 606/153 |
| 2002/0087175 A1 * | 7/2002 | Gifford et al. | 606/153 |
| 2002/0151914 A1 * | 10/2002 | Gifford et al. | 606/153 |
| 2004/0015178 A1 * | 1/2004 | Monassevitch et al. | 606/153 |
| 2004/0015179 A1 | 1/2004 | Monassevitch et al. | |
| 2005/0059997 A1 | 3/2005 | Bauman et al. | |
| 2005/0070934 A1 * | 3/2005 | Tanaka et al. | 606/153 |
| 2005/0184121 A1 * | 8/2005 | Heinrich | 227/175.1 |
| 2005/0283191 A1 * | 12/2005 | Fontayne et al. | 606/219 |
| 2006/0253141 A1 | 11/2006 | Ortiz et al. | |

FOREIGN PATENT DOCUMENTS

| | | |
|---|---|---|
| SU | 1186199 A | 10/1985 |
| WO | WO 81/00046 | 1/1981 |

\* cited by examiner

COMPRESSION ANASTOMOSIS RING ASSEMBLY AND APPLICATOR FOR USE THEREWITH

FIELD OF THE INVENTION

The present invention relates to a compression anastomosis ring assembly and an applicator for use therewith in endoluminal anastomosis surgical procedures.

DEFINITION

Throughout the specification and claims below, the terms below will be used with the following meanings:

Anastomosis: a surgical restoration of the continuity of a hollow organ which has been separated.

Proximal: situated close to the user.

Distal: situated distant or away from the user (relative to proximal).

BACKGROUND OF THE INVENTION

Excision of a segment of diseased colon or intestine and subsequent anastomosis of the cut end portions is known in the art. Such excision and anastomosis can be carried out by entering the abdominal cavity using either open surgery or a laparoscopic procedure. However, there are significant problems associated with these procedures.

The integrity of the anastomosis must be sound so that there is no risk of the anastomosis rupturing or leaking into the abdominal cavity. Opening the bowel lumen and exposing the clean abdominal cavity to contamination increases the risk of postoperative infection. There have been a number of improvements in anastomosis procedures over the past decade. These improvements can be found inter alia in U.S. Pat. No. 5,197,648 to Gingold; U.S. Pat. No. 5,312,024 to Grant, et al.; U.S. Pat. No. 5,344,059 to Green, et al.; U.S. Pat. No. 5,411,508 to Bessler, et al.; and U.S. Pat. No. 5,639,008 to Gallagher, et al.

In order to avoid opening the bowel lumen and exposing the clean abdominal cavity to endoluminal contents, intussusception of the colon or intestine may be employed. Intussusception enables the excision to be conducted within an apparatus preventing contamination of the body cavity. There has been a development recently whereby the intussusception, anastomosis and resection of the intussuscepted segment is facilitated by an apparatus and method discussed in U.S. Pat. No. 6,117,148 to Ravo et al.

Each of the foregoing inventions utilizes stapling for achieving anastomosis of the portions of bowel or intestine to be joined. It would be advantageous to utilize a procedure and apparatus that did not rely on applying a plurality of staples or other connecting devices, which, of necessity, remain in the bowel and which, despite the utmost care by the surgeon, may leak or rupture.

Surgical fastening clips are known in the art. The clips apply a clamping force to a site, such as a blood vessel, thereby reducing its cross-sectional area. Surgical fastening clips known in the art are sometimes formed of a shape-memory alloy which deform to a closed configuration when heated. The clamping force applied by the clip is increased as it is heated. Typical surgical clips are discussed in, for example, U.S. Pat. No. 5,171,252 to Friedland; EP 0,326,757 to Fujitsuka Tatsuo; and SU 1,186,199 to Makarov et al.

A major disadvantage of known shape-memory alloy clips is that they permit compression of only approximately 80-85% of the junction perimeter. This requires the use of additional manual sutures, which reduce the integrity of the seal of the junction during the healing period and its elasticity during the post-operative period. Additional suturing is also problematic since it has to be carried out across a join which includes a portion of the clip, thereby rendering difficult the sealing and anastomosis of the organ portions. Furthermore, once in place, prior art clips require further surgery to be performed, namely, incisions through tissue so as to create a passageway between the two organ portions which have been joined by the clip. This is further discussed in U.S. Pat. No. 6,402,765 to Monassevitch et al. and U.S. Pat. No. 6,896,684 to Monassevitch et al.

The surgical clip and the anastomosis clip applicator device, recited in U.S. Pat. No. 6,402,765 and U.S. Pat. No. 6,896,684 respectively, relate to a shape-memory alloy clip insertable through apertures formed in the side-walls of a pair of adjacent hollow organ portions utilizing an anastomosis clip applicator device. Access to the hollow organ is generally extra-tubular, that is, achieved by means of open surgery or a laparoscopic procedure during which access to the organ parts results in the risk of exposure of the abdominal cavity to contamination from the excised or severed organ. Furthermore, the nature of the anastomosis provides a join of the organ portions through the adjacent side-walls. Generally, a join formed of the in-line excised ends is preferred. This arrangement avoids the possibility of resistance to or reduction in the flow through the anastomosed adjacent organ portions.

Recently, U.S. Pat. No. 6,884,250 to Monassevitch et al. and U.S. patent application Ser. No. 10/237,505 to Monassevitch et al. describe endoluminal intussusception and anastomosis devices which apply surgical clips to an intussuscepted and anastomosed region of a lumen with the clip being delivered endoluminally. The apparatuses described in these documents have, in practice, a limiting minimum external diameter which substantially restricts their application.

Other forms of clips and/or anastomosis devices are discussed in U.S. Pat. No. 4,957,499 to Lipstov et al.; U.S. Pat. Nos. 4,476,863 and 4,567,891 to Kanshin et al.; Soviet Pat. No. SU 79-00049 to Kanshin et al.; U.S. Pat. No. 4,505,272 to Utyamshev et al.; and Wullstein et al. *Compression anastomosis (AKA-2) in colorectal surgery: results in* 442 *consecutive patients*; British Journal of Surgery, (2000) 87, 1071-1075, Blackwell Science Ltd. 2000. In these publications the force used to effect anastomosis is not necessarily constant and is dependent on the thickness of the tissue of the organ to undergo anastomosis. Accordingly, the resulting join is weak or incomplete.

Therefore, there still exists a need for a surgical apparatus which allows for endoluminal insertion into organ lumens, including transanal insertion, as well as insertion into small lumens, such as that of the esophagus. Such endoluminal insertion would obviate the need for additional surgical procedures, such as enterotomies, which are often accompanied by manual sutures. This would greatly assist in a smooth robust seal of the wound junction during the healing period, as well as preserve its elasticity during the post-operative period.

SUMMARY OF THE INVENTION

It is an object of the present invention to provide a compression anastomosis ring (CAR) assembly for use in anastomosis surgical procedures.

It is yet another object of the present invention to provide a compression anastomosis ring (CAR) assembly for use in anastomosis surgical procedures wherein compression is provided by an element of the assembly formed of a shape-memory alloy.

It is another object of the present invention to provide a CAR assembly and applicator that can have reduced dimensions, thereby extending the range of application of the assembly and applicator. Use of the assembly increases the quality of the luminal anastomosis by providing a substantially liquid-tight seal and thereby promoting hemostasis.

It is a further object of the present invention to provide an applicator for applying a compression anastomosis ring (CAR) assembly constructed according to the present assembly in anastomosis surgical procedures.

Another object of the present invention is to provide a method for using the compression anastomosis ring (CAR) assembly taught herein.

There is therefore provided in one aspect of the present invention a compression anastomosis ring (CAR) assembly. The assembly comprises a first and second portion with the first portion comprising an anvil disk. The second portion comprises a bottom ring positioned substantially parallel to and spaced apart from the anvil disk; one or more ring elements, where one of the one or more ring elements is a needle ring positioned on a side of the bottom ring distal from the anvil disk, the needle ring having a plurality of needles extending generally transversely in the direction of the anvil disk; and one or more spring elements formed at least partially of a shape-memory alloy, the spring elements positioned on one of the one or more ring elements and being in compressive force transmissive contact with the bottom ring. When the compression anastomosis ring (CAR) assembly is positioned so as to hold tissue sections to be joined by anastomosis between the anvil disk and the bottom ring, the plurality of needles is operative, in response to a force provided by an applicator, to pierce the tissue sections and the disk. This holds the bottom ring in mechanical connection with the disk. Anastomosis is effected by a relatively constant force applied to the bottom ring by the one or more spring elements.

In one embodiment of the assembly, the one or more spring elements are positioned on the needle ring so as to be in compressive force transmissive contact with the bottom ring.

In another embodiment of the CAR assembly, the one or more ring elements are comprised of two ring elements, the needle ring and a compression anastomosis flange (CAF) formed as a ring and positioned inside the bottom ring. In some instances of this embodiment, the CAF is positioned between the needle ring and the bottom ring and the one or more spring elements are positioned on the compression anastomosis flange (CAF) so as to be in compressive force transmissive contact with the bottom ring.

The anvil disk in the assembly is made from a polymeric material and has a substantially ring-shaped outer portion integrally formed with an inner core. The needles are operable to penetrate and pass through the disk in response to a predetermined force applied to the needle ring. In some embodiments of the assembly, the anvil disk includes a plurality of holes in apposition to and in registration with the plurality of needles. This allows entry of the needles and passage through the anvil disk in response to a predetermined force applied to the needle ring.

In yet another embodiment of the CAR assembly, the one or more spring elements are brought to their compressed configuration and the alloy from which they are formed to its martensitic state by positioning the CAR assembly on a CAR applicator before bringing the tissue to be joined by anastomosis between the anvil disk and the bottom ring. In some instances of this embodiment, the one or more spring elements are brought to their compressed configuration and the alloy from which they are formed to its martensitic state by applying a compressive stress. In other instances, the one or more spring elements are brought to their compressed configuration and the alloy from which they are formed to its martensitic state by cooling and then applying a compressive stress.

In yet another aspect of the present invention, there is provided an endoluminal anastomosis apparatus for joining preselected organ wall portions of a hollow organ. The apparatus includes a compressive anastomosis ring assembly and an endoluminal CAR applicator. The compressive anastomosis ring (CAR) assembly comprises a first and second portion with the first portion comprising an anvil disk. The second portion comprises a bottom ring positioned substantially parallel to and spaced apart from the anvil disk; one or more ring elements, where one of the one or more ring elements is a needle ring positioned on a side of the bottom ring distal from the anvil disk, the needle ring having a plurality of needles extending generally transversely in the direction of the anvil disk; and one or more spring elements formed at least partially of a shape-memory alloy, the spring element positioned on one of the one or more ring elements and being in compressive force transmissive contact with the bottom ring. When the compression anastomosis ring (CAR) assembly is positioned so as to hold tissue sections to be joined by anastomosis between the anvil disk and the bottom ring, the plurality of needles is operative, in response to a force provided by an applicator, to pierce the tissue sections and the disk. This holds the bottom ring in mechanical connection with the disk. Anastomosis is effected by a relatively constant force applied to the bottom ring by the one or more spring elements. The endoluminal CAR applicator of the apparatus has a proximal end and a distal end. The applicator comprises: i) attachment means including an anvil rod extendable from the applicator, adapted to attach and hold the anvil disk thereto and operable to move the attached anvil disk toward the second portion of the CAR assembly; ii) deployment means positioned on the distal end of the applicator and operable to deploy the second portion of the CAR assembly positioned thereon so that the one or more spring elements may be compressed and so that the plurality of needles may be brought to a position where they pierce the anvil disk and the tissue sections to be joined by anastomosis; iii) a blade element positioned in spaced relationship with the deployment means, the blade element operable to cut through the anvil disk and the tissue sections held between the anvil disk and the bottom ring of the assembly, subsequent to operation of the deployment means so as to deploy the second portion of the CAR assembly and operation of the attachment means so as to bring the anvil disk in proximity to the bottom ring; and iv) one or more activators, each activator operationally connected to one or more of the deployment means, the attachment means and the blade element for activating the attachment means, the deployment means and the blade element.

In an embodiment of the apparatus, the one or more spring elements are positioned on the needle ring so as to be in compressive force transmissive contact with the bottom ring.

In yet another embodiment of the apparatus, the one or more ring elements are two or more ring elements. One of the two or more ring elements is the needle ring and another of the ring elements is a compression anastomosis flange (CAF) formed as a ring and positioned inside the bottom ring. In instances of this embodiment, the CAF is positioned between the needle ring and the bottom ring. The one or more spring elements are positioned on the compression anastomosis flange (CAF) so as to be in compressive force transmissive contact with the bottom ring.

The anvil disk in the apparatus is made from a polymeric material and has a substantially ring-shaped outer portion integrally formed with an inner core. When the blade element cuts through the anvil disk, the disk's outer ring-shaped portion is severed from the inner core and detached from the attachment means. The outer ring-shaped portion is then held to the bottom portion by the plurality of needles so that the outer ring-shaped portion is in registration with the bottom ring. This allows the outer ring-shaped portion to serve as an anvil for the bottom ring when the one or more spring elements press on the bottom ring compressing the tissue held therebetween.

In yet another embodiment of the apparatus, the deployment means further comprises a load means positioned in force transmissive contact with the deployment means so that when the one or more spring elements are deployed, the load means exerts a load on the one or more spring elements thereby bringing these elements to their compressed configuration. The alloy from which the spring elements are formed is also brought to its martensitic state. In some instances of this embodiment, the one or more spring elements are cooled before the load means exerts a load on, and compresses, the one or more spring elements.

In a further aspect of the present invention there is provided a method for joining severed tissue by anastomosis. The method comprises the steps of: positioning the severed tissue between the first and second portions of a compressive anastomosis ring (CAR) assembly, the assembly operable for joining the severed tissue by an anastomosis surgical procedure; moving the first portion in close proximity to the second portion so as to hold the severed tissue therebetween; and compressing the tissue through use of one or more shape-memory alloy spring elements positioned in force transmissive proximity to the second portion of the CAR assembly and operable to generate a restorative force. The shape-memory alloy spring elements are in force transmissive contact with a bottom ring of the second portion, the bottom ring in turn in force transmissive contact with the held tissue.

In an embodiment of the method, the method further includes the step of cutting the compressed tissue and cutting through an anvil disk of the first portion of the CAR assembly.

In another embodiment of the method, the CAR assembly comprises a first and second portion with the first portion comprising an anvil disk. The second portion comprises a bottom ring positioned substantially parallel to and spaced apart from the anvil disk; one or more ring elements, where one of the one or more ring elements is a needle ring positioned on a side of the bottom ring distal from the anvil disk, the needle ring having a plurality of needles extending generally transversely in the direction of the anvil disk; and one or more spring elements formed at least partially of a shape-memory alloy, the spring element positioned on one of the one or more ring elements and being in compressive force transmissive contact with the bottom ring. When the compression anastomosis ring (CAR) assembly is positioned so as to hold tissue sections to be joined by anastomosis between the anvil disk and the bottom ring, the plurality of needles is operative, in response to a force provided by an applicator, to pierce the tissue sections and the disk. This holds the bottom ring in mechanical connection with the disk. Anastomosis is effected by a relatively constant force applied to the bottom ring by the one or more spring elements.

In yet another embodiment of the method, prior to the step of compressing, the method further includes the step of deploying the one or more shape-memory alloy spring elements when they are in their compressed configuration, the alloy from which they are formed being in its martensitic state. The martensitic state of the alloy of the deployed one or more spring elements is a martensitic state selected from a group of states consisting of the stress-retained martensitic state and the stress-induced martensitic state.

In yet another embodiment of the method, the method further includes the step of deploying the one or more shape-memory alloy spring elements in their non-compressed configuration, the alloy from which the spring elements are formed being in its austenite state.

BRIEF DESCRIPTION OF THE DRAWINGS

The present invention will be more fully understood and its features and advantages will become apparent to those skilled in the art by reference to the ensuing description, taken in conjunction with the accompanying drawings, in which.

Similar elements in the Figures are numbered with similar numerals.

DETAILED DESCRIPTION OF THE INVENTION

The incidence of tumors, ulcers, inflammation and other traumas and lesions in the lower large intestine and in other sections of the gastrointestinal tract is high. Excising a diseased section of bowel includes a risk of contaminating the abdominal cavity by discharge of digested material from the exposed bowel interior. A risk of leakage or rupture at the join or at the posterior constriction of the anastomosis lumen also exists after joining the open ends of the two bowel portions subsequent to excising a section of bowel between them.

The present invention provides a solution to both problems by describing an assembly and apparatus for an improved joining technique. Joining or anastomosis of the cut ends of bowel tissue from which tissue has been excised is accomplished using a compression anastomosis ring (CAR) assembly. A CAR applicator for applying the assembly is also described.

The compression anastomosis ring (CAR) assembly includes an anvil disk and a bottom ring where, in operation, the latter is compressed against the former. Compression is effected by spring elements formed from a shape-memory alloy positioned on an element in mechanical association with the bottom ring. The CAR detaches from the site of anastomosis when anastomosis is complete and is naturally expelled through the anus when the tissue undergoing anastomosis is bowel tissue. The applicator delivering the CAR is constructed to cut the ends of the excised bowel so that anastomosis with the CAR is effected cleanly. The fastening apparatus of the present invention may be used to achieve anastomosis following either conventional or laparoscopic excision of a diseased intestinal portion.

The anastomosis apparatus of the present invention is described herein as being used to join bowel tissue from which an excised portion has been removed. It should be evident that the device of the present invention may, with little or no modification, be used with tissue of other organs as well. Such other organs include, but are not limited to, the esophagus and stomach.

Similarly, it should be readily apparent to one skilled in the art that the device and method of the present invention can be used to effect anastomosis on tissue of animals as well as humans, particularly, but without being limiting, other mammalian species.

Figure 1:
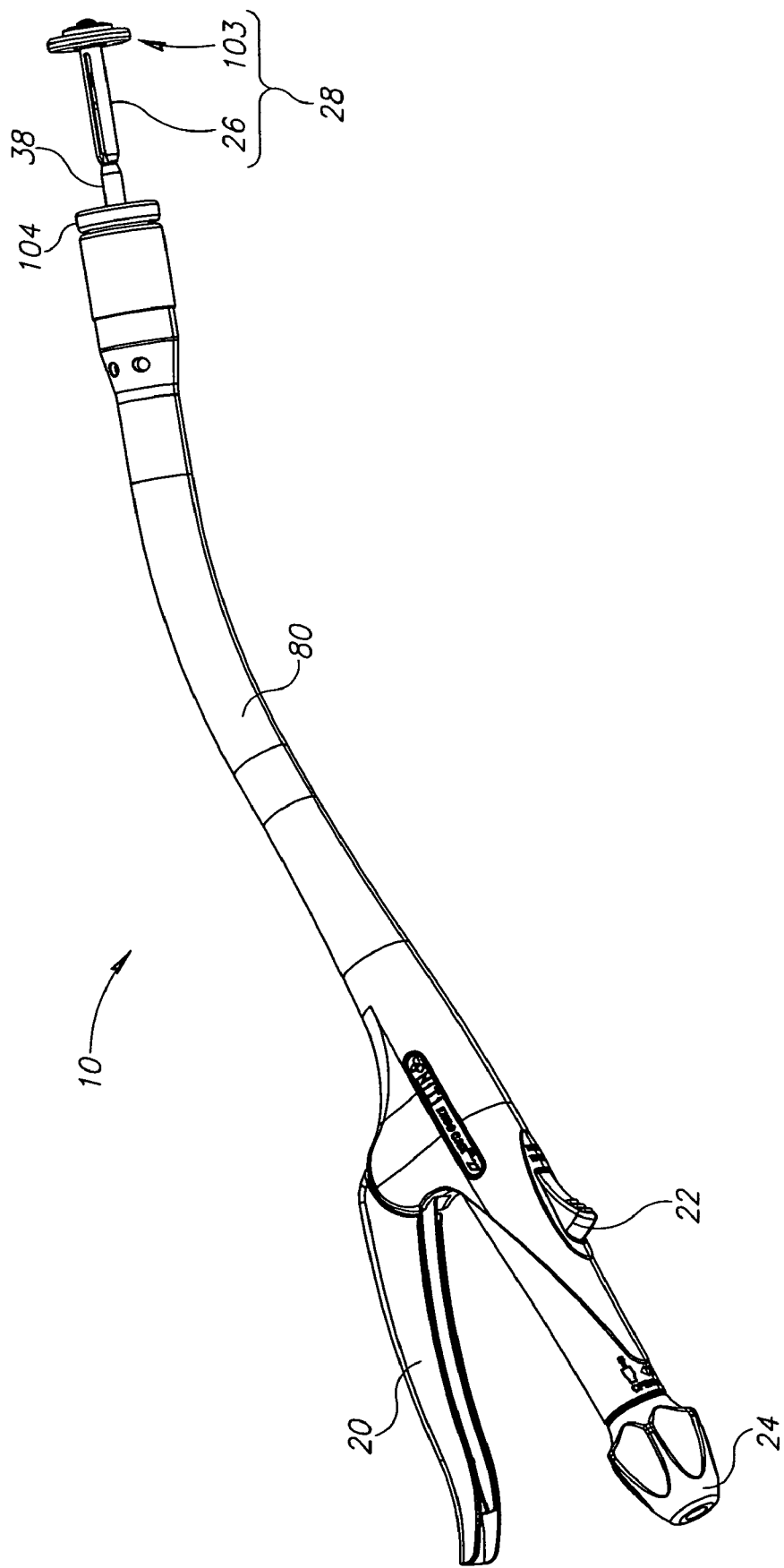
FIG. 1 illustrates a side view of a compression anastomosis ring (CAR) applicator usable with a CAR assembly constructed according to the present invention.

Reference is now made to FIG. 1 in which is shown an overview of a typical CAR applicator 10 suitable for applying a CAR assembly 100 (best seen in FIG. 7 below) constructed according to the present invention for use in anastomosis surgical procedures. Applicator 10 consists of an elongated housing 80 at the proximal end of which is situated a control knob 24, a lever 20, and a cut trigger 22. At the distal end of CAR applicator 10 is situated an anvil assembly 28 which includes an anvil disk 103 of CAR assembly 100 and an anvil rod 26. Anvil assembly 28 connects to applicator 10, an endoluminal anastomosis apparatus, by a trocar 38. A bottom ring 104 of CAR assembly 100 is affixed directly to the distal end of CAR applicator 10.

Figure 2:
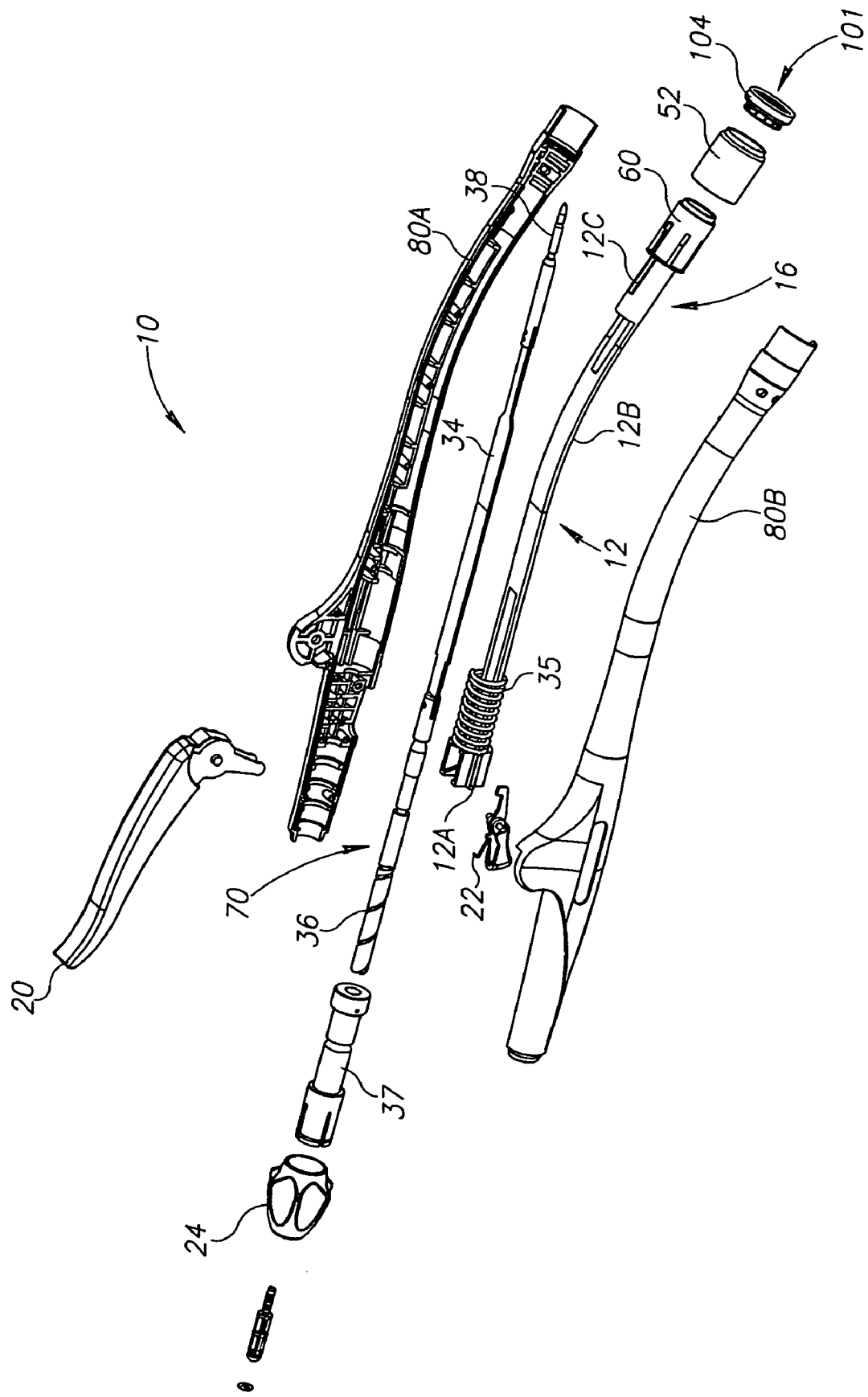
FIG. 2 shows an exploded view of the CAR applicator shown in FIG. 1.

An exploded view of applicator 10 is shown in FIG. 2 to which reference is now made. The exploded view shows a view of housing 80, its halves denoted as 80A and 80B. Additionally, central member 70 is shown, the member having control knob 24 positioned at its proximal end and trocar 38 at its distal end. Joined to trocar 38 is trocar connecting link 34 which in turn is in mechanical communication with helix 36 which itself is in mechanical communication with knob shaft 37. Shaft 37 is controlled by control knob 24 which allows for the advance or retraction of trocar 38.

Central member 70 is inserted into blade pusher assembly 16, the latter includes blade pusher 12. Blade pusher 12 has a proximal end 12A connected to its distal end 12C by linking section 12B. The proximal end 12A of blade pusher 12 is in mechanical communication with main spring 35. At the distal end 12C of blade pusher 12 are other elements of blade pusher assembly 16. At distal end 12C a step slider 60 is positioned and it is sized and configured to be inserted into ring support 52. Bottom ring 104 of CAR assembly 100 is configured and sized to fit onto ring support 52. Anvil assembly 28 which includes anvil disk 103 (not shown in FIG. 2 but shown in FIG. 1) of CAR assembly 100 is sized and configured to sit on trocar 38 when central member 70 is positioned inside blade pusher assembly 16 and when trocar 38 has been advanced past the distal end of blade pusher assembly 16.

For ease of understanding, housing 80 of FIG. 1 is shown as split into two halves 80A and 80B in FIG. 2. It should be noted that the two halves of housing 80 shown in FIG. 2 are in effect two parts that fit around blade pusher assembly 16 and central member 70 after the latter has been inserted into the former. After being connected, the two halves act as a single integrated part.

Operation of the elements described above will be described more fully below in conjunction with other Figures yet to be discussed.

Figure 3:
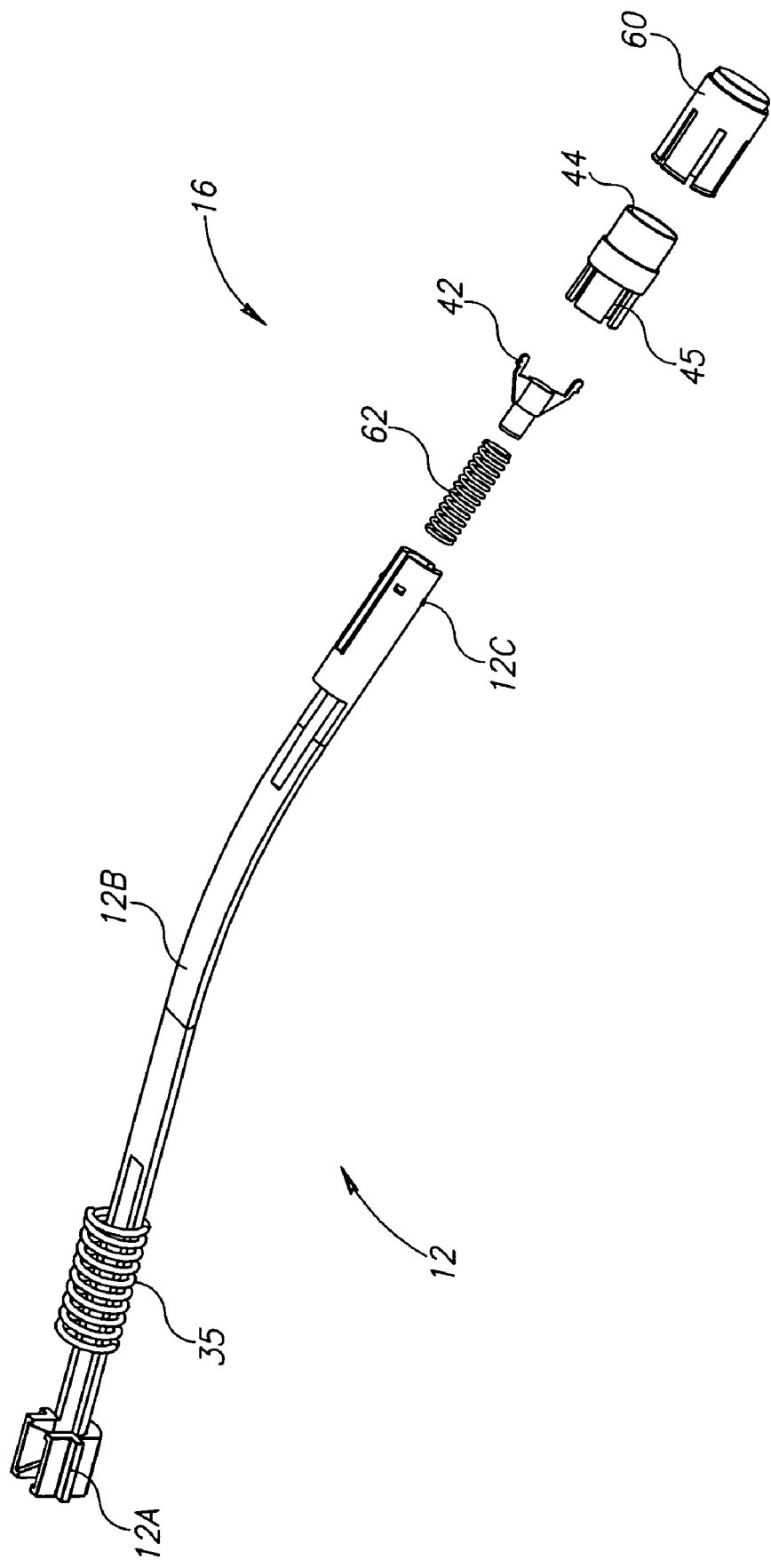
FIG. 3 shows an enlarged, partially exploded, view of the blade pusher assembly of the applicator shown in FIGS. 1 and 2.

Reference is now made to FIG. 3 in which an expanded view of blade pusher assembly 16 is shown. Blade pusher 12 allows for advancing or retracting blade element 44. Proximal end section 12A of blade pusher 12 of blade pusher assembly 16 is joined to its distal substantially cylindrical end 12C by linking section 12B. Blade pusher 12 of blade assembly 16 is comprised of a distal end section 12C which engages with a blade holder 45. When blade pusher 12 moves in the direction of its distal end, an anvil lock spring 62, positioned inside the substantially cylindrical distal end 12C of blade pusher 12 pushes against an anvil lock 42. The latter is positioned to lie against spring 62. Anvil lock 42 moves toward, and stops at, blade holder 45 which is mechanically and operationally in communication with blade element 44. Substantially cylindrical blade element 44 and blade holder 45 are positioned inside substantially cylindrical step slider 60 which in turn is positioned inside substantially cylindrical ring support 52 (shown for example in FIGS. 2 above and 8B below) forming essentially concentric cylindrical shells centered on trocar 38 (FIG. 2). Further operation of the step slider 60, the blade element 44 and the blade holder 45 will be described below in conjunction with FIGS. 9A-13.

Figure 4:
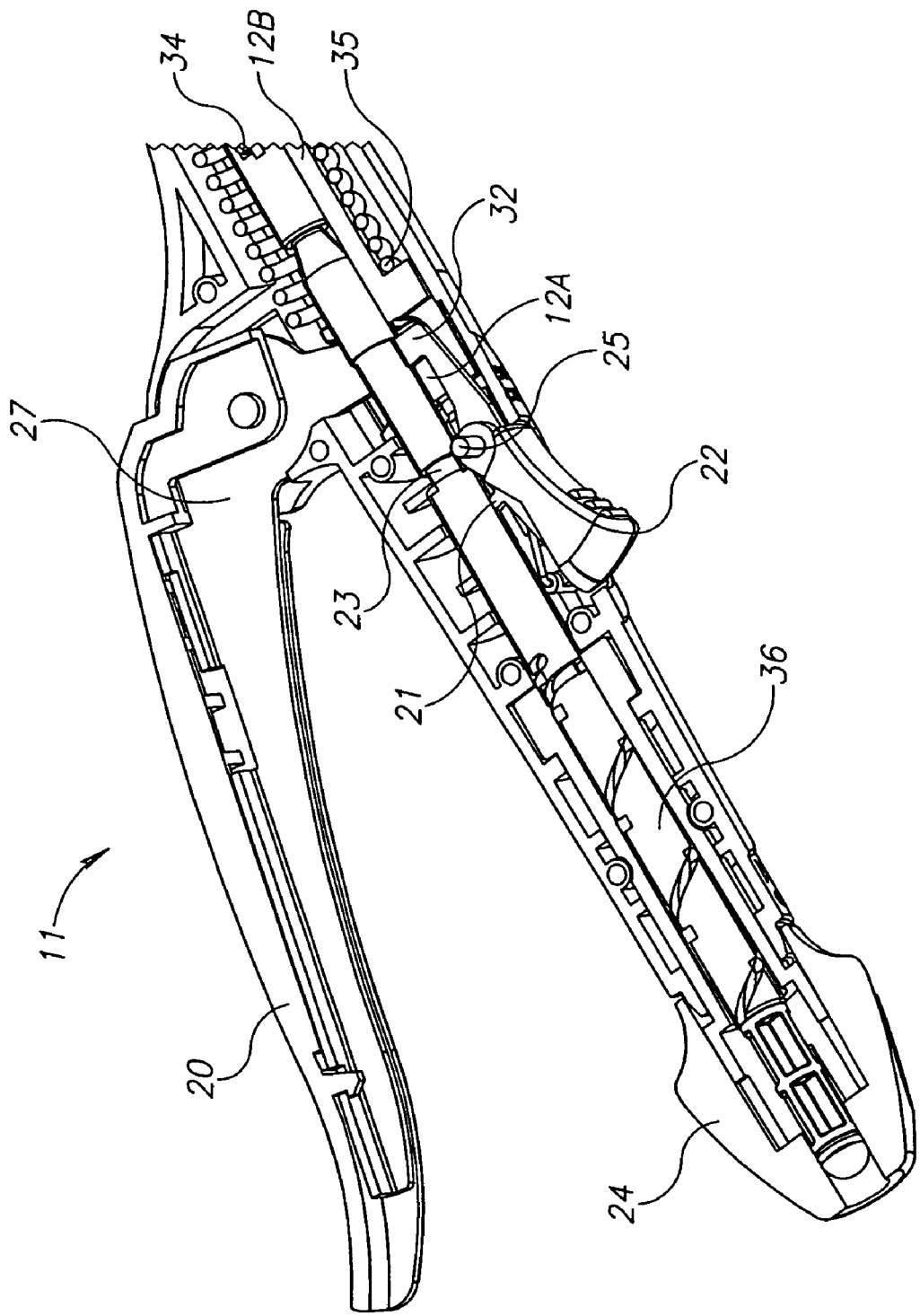
FIGS. 4 and 5 show an enlarged view of the proximal end of the CAR applicator shown in FIGS. 1 and 2 before and after activating the cut trigger of the applicator, respectively.
Figure 5:
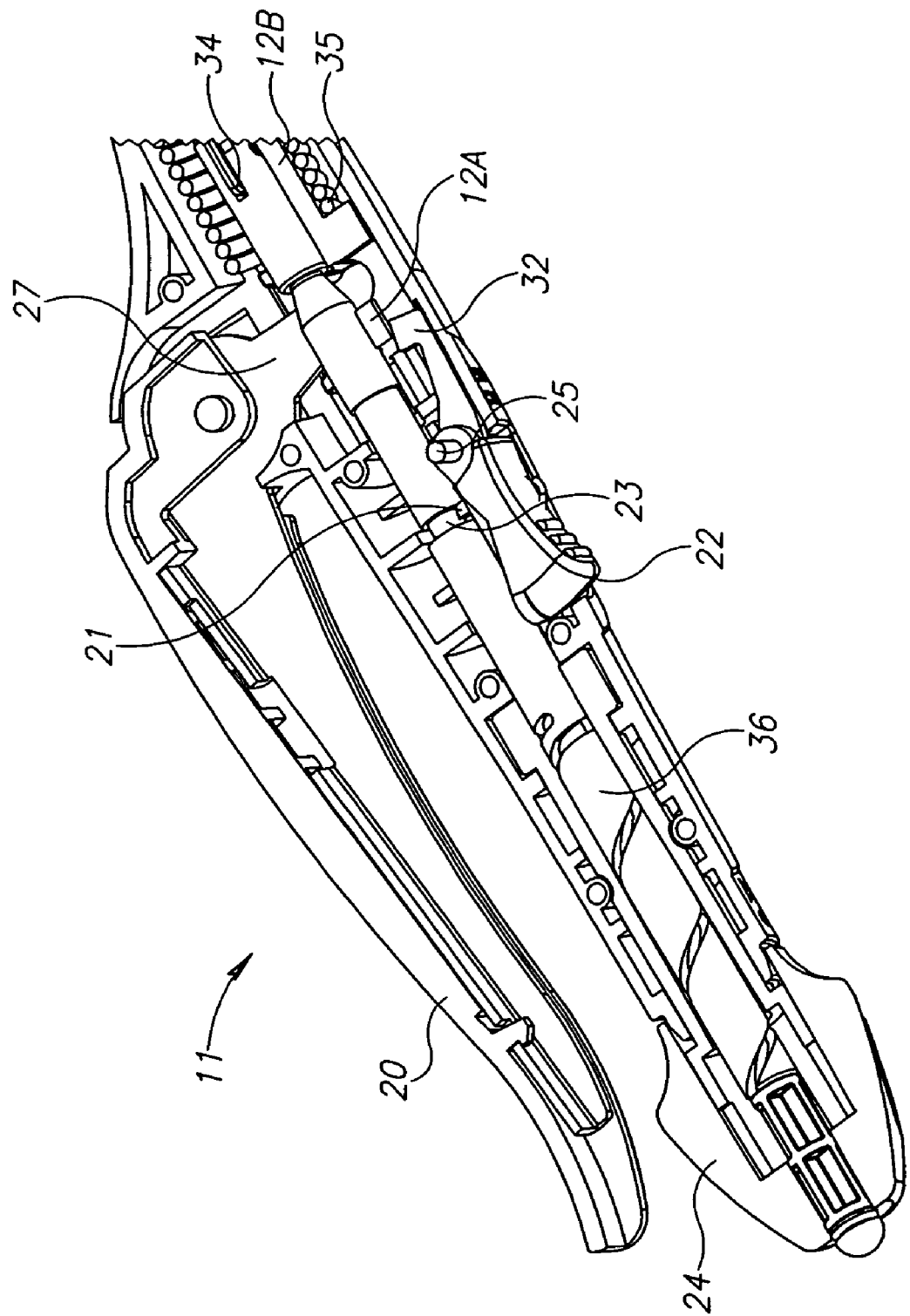

Reference is now made to FIGS. 4 and 5 in which the proximal end 11 of CAR applicator 10 is shown both before and after activation of cut trigger 22, respectively. The activation of cut trigger 22 and the squeezing of lever 20 allow blade element 44 (discussed in conjunction with FIG. 3 above and to be discussed again in conjunction with FIGS. 9A-13 below) to move up and cut tissue held between anvil disk 103 (FIG. 1) and bottom ring 104 (FIG. 1) of CAR assembly 100 to be described in greater detail in conjunction with FIGS. 6-7 below. When cut trigger 22 is pressed, cut trigger pin 21 moves out of cut slot 23 on helix 36. Cut trigger arm 32 moves downwardly away from the proximal end 12A of blade pusher 12 allowing lever 20 to be squeezed.

Lever 20 is in mechanical communication with the proximal end 12A of blade pusher 12 via lever arm 27. Arm 27 is positioned in and engages with the pocket formed at proximal end 12A of blade pusher 12. This pocket is best seen in FIG. 3. When lever 20 is squeezed, lever arm 27 rotates so that it moves and pushes blade pusher 12 (FIG. 3) bringing blade element 44 (FIG. 3) to its cutting position. As lever arm 27 pushes blade pusher 12 at its proximal end 12A, main spring 35 compresses. Compressed main spring 35 pushes proximal end 12A of blade pusher 12 in the direction of knob shaft 37

(best seen in FIG. 2) causing blade pusher 12 to return to its initial position after the cutting operation of CAR applicator 10 has ended.

Figure 6:
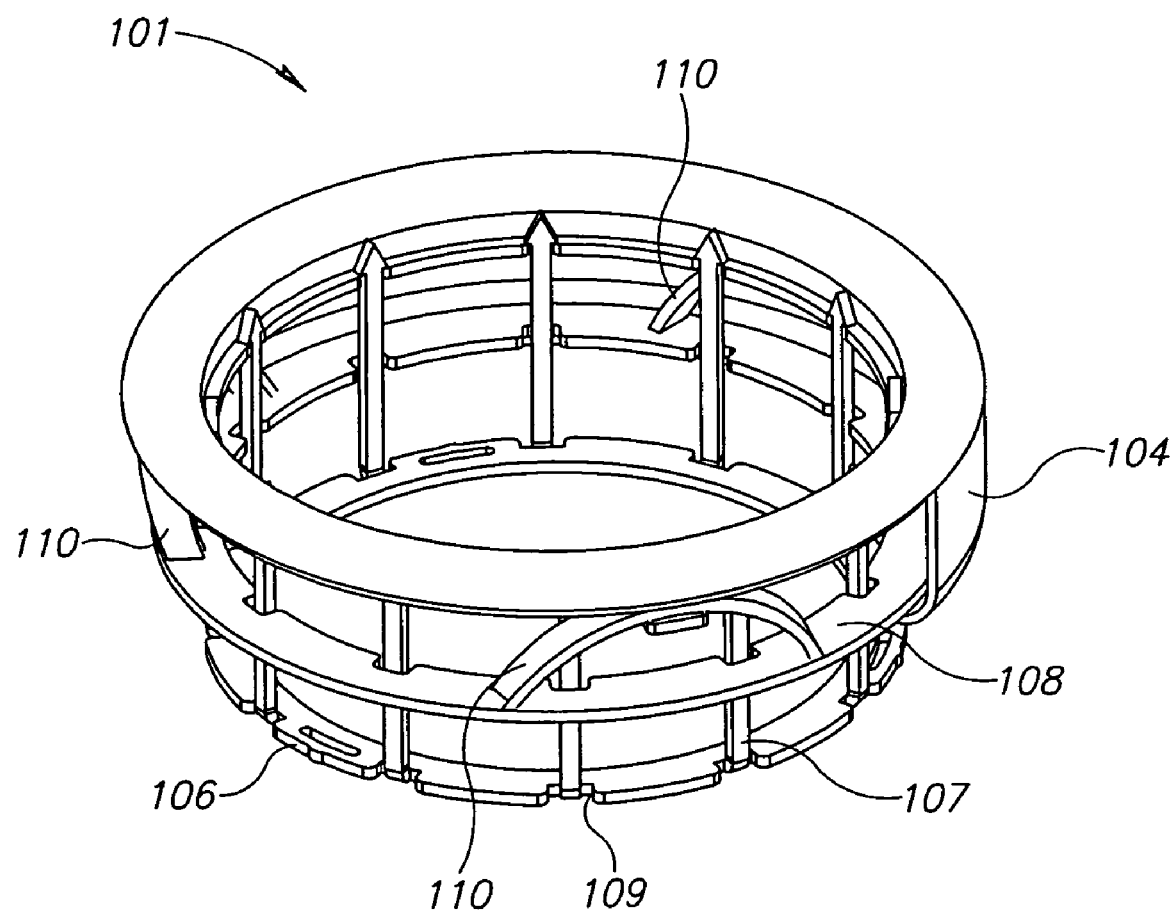
FIG. 6 shows an isometric view of the second portion of the CAR assembly constructed according to an embodiment of the present invention.
Figure 7:
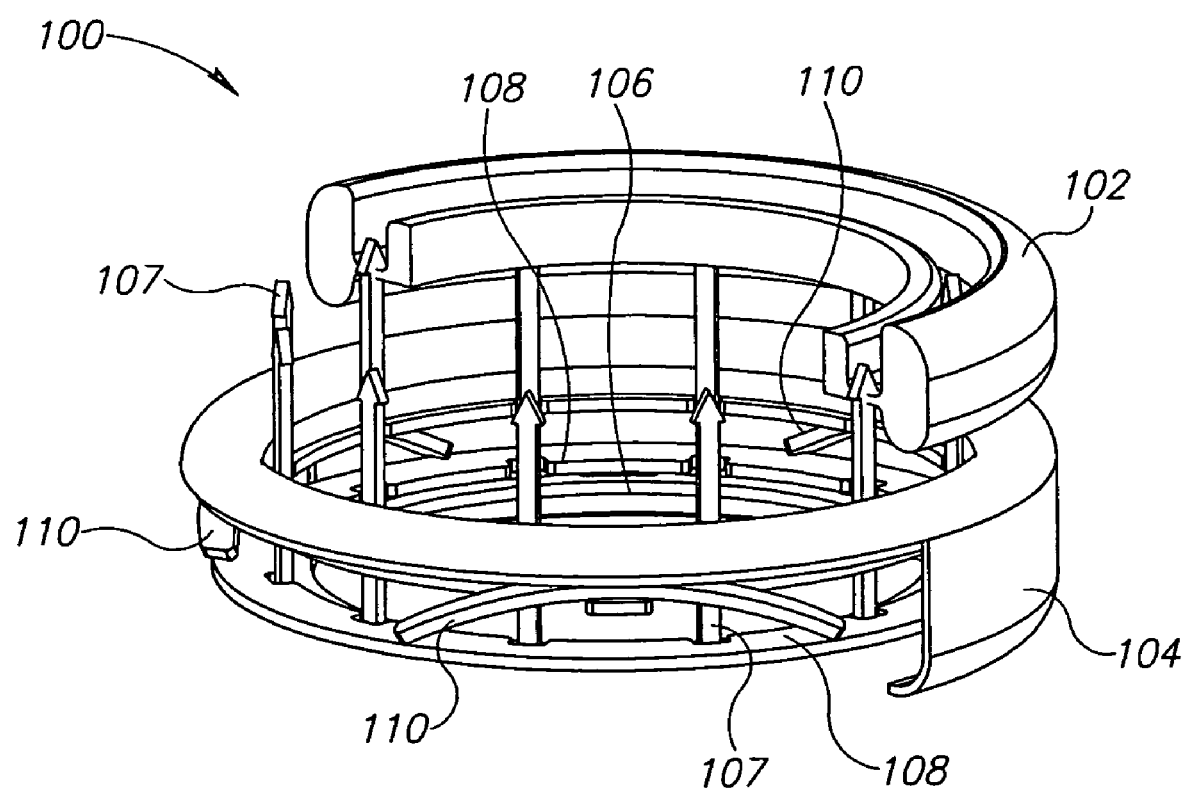
FIG. 7 shows an isometric view of the entire CAR assembly constructed according to an embodiment of the present invention.

Reference is now made to FIGS. 6 and 7 where partial cut-away side views of CAR assembly 100 are shown. FIG. 6 represents a cut away view of only the second portion 101 of CAR assembly 100. The entire CAR assembly 100 is shown in FIG. 7. CAR assembly 100 includes an anvil disk 103 (FIGS. 9A and 10A) formed of any of a large number of rigid plastics known to those skilled in the art and a bottom ring 104 which may be formed from any of a large number of plastics or metals known to those skilled in the art. Anvil disk 103 is formed to be comprised of an anvil ring 102 positioned on the disk's periphery and an anvil inner core 105 (the latter easily seen, for example, in FIGS. 9A and 10A). Anvil disk 103 may include holes into which the ends of needles 107, to be discussed below, may enter. Alternatively, no such holes need be included and needles 107 themselves pierce and enter plastic anvil disk 103 when a force of sufficient magnitude is exerted on them.

Bottom ring 104 girdles a needle ring 106 (partially obscured in FIG. 7 but readily visible in FIG. 6), CAR flange 108 and one or more spring elements 110. Needle ring 106 includes a plurality of barbed needles 107, each needle 107, typically but without intending to limit other possibilities, spaced substantially equidistant from its two nearest neighbors. Needles 107 are deployed in essentially a circular configuration to conform to the circumference of needle ring 106. Again such a configuration is exemplary only and not intended to be limiting.

Needles 107 may be formed integrally with needle ring 106. Alternatively, they may be joined to needle ring 106 by any of several methods known to those skilled in the art, such as welding, gluing, and pressure fitting. These methods are exemplary only and are not intended to be limiting. The shape of the barbs on the heads of needles 107 as shown in FIGS. 6 and 7 is exemplary only. Any generally penetrating shape may be used as the head of needles 107, even sharp heads without barbs.

CAR flange 108 is typically, but without intending to be limiting, formed from any of a large number of metals or plastics known to those skilled in the art. Needle ring 106 and the plurality of barbed needles 107 are typically, but without intending to be limiting, formed from any of a large number of metals or plastics known to those skilled in the art. The one or more spring elements 110 are made from a shape-memory alloy, typically, but again without intending to be limiting, nitinol. Also typically, but without intending to be limiting, spring elements 110, when in their unloaded austenite state, are arch-shaped. The spring elements are positioned to lie on CAR flange 108 between flange 108 and bottom ring 104. The top of the arch contacts the underside, that is the closest side, of bottom ring 104. When the shape-memory alloy from which spring elements 110 are formed is in its loaded stress-induced martensite state (or stress-retained martensite state), spring elements 110 lie substantially flat along CAR flange 108 below bottom ring 104. Spring elements 110 are positioned on CAR flange 108 so that their ends can move when going from the spring elements' uncompressed arched shape to the spring elements' flat compressed shape and vice versa.

Needle ring 106 is positioned below CAR flange 108. CAR flange 108 has indentations 109 along its inner generally circular circumference through which barbed needles 107 extend from needle ring 106 past CAR flange 108.

Spring elements 110 have been described herein as having an arched uncompressed configuration when not compressed and a flat configuration when compressed; these are essentially leaf springs. The present invention also contemplates other possible spring forms and configurations, including conventional coiled configurations.

In what has been described herein throughout, CAR assembly 100 has been described as having a separate CAR flange 108 and a needle ring 106. In other embodiments, there may be only a single element, essentially the needle ring with needles 107 affixed thereon. The CAR flange may be eliminated. In such an embodiment, spring elements 110 are positioned on the needle ring and they contact the bottom of bottom ring 104. The spring elements are movable on needle ring 106 and they are capable of moving from their compressed to uncompressed configurations/shapes and vice versa. In this latter embodiment, spring elements 110 are typically, but without intending to be limiting, deployed in their non-compressed austenitic state. When a CAR flange 108 is employed the spring elements 110 are typically deployed in their compressed martensitic state.

It should be noted that all ring or ring-shaped elements discussed herein, including the claims, with respect to the CAR assembly 100, contemplate, in addition to the use of circular-shaped elements, the possibility of using elliptical, oval or other shaped elements. The use of "ring" should not be deemed as shape limiting for the rings elements described and illustrated hereinabove. These ring elements include, but are not limited to, the needle ring 106, the CAR flange 108, and the bottom ring 104.

It should also be noted that the use of the term "bottom ring" as a term for element 104 should not be deemed as denoting anything about the specific spatial and functional relationship between this element and the other elements of the CAR assembly 100. The spatial and functional relationship of element 104 and the other elements of assembly 100 are defined by the description and the drawings.

Figure 8A:
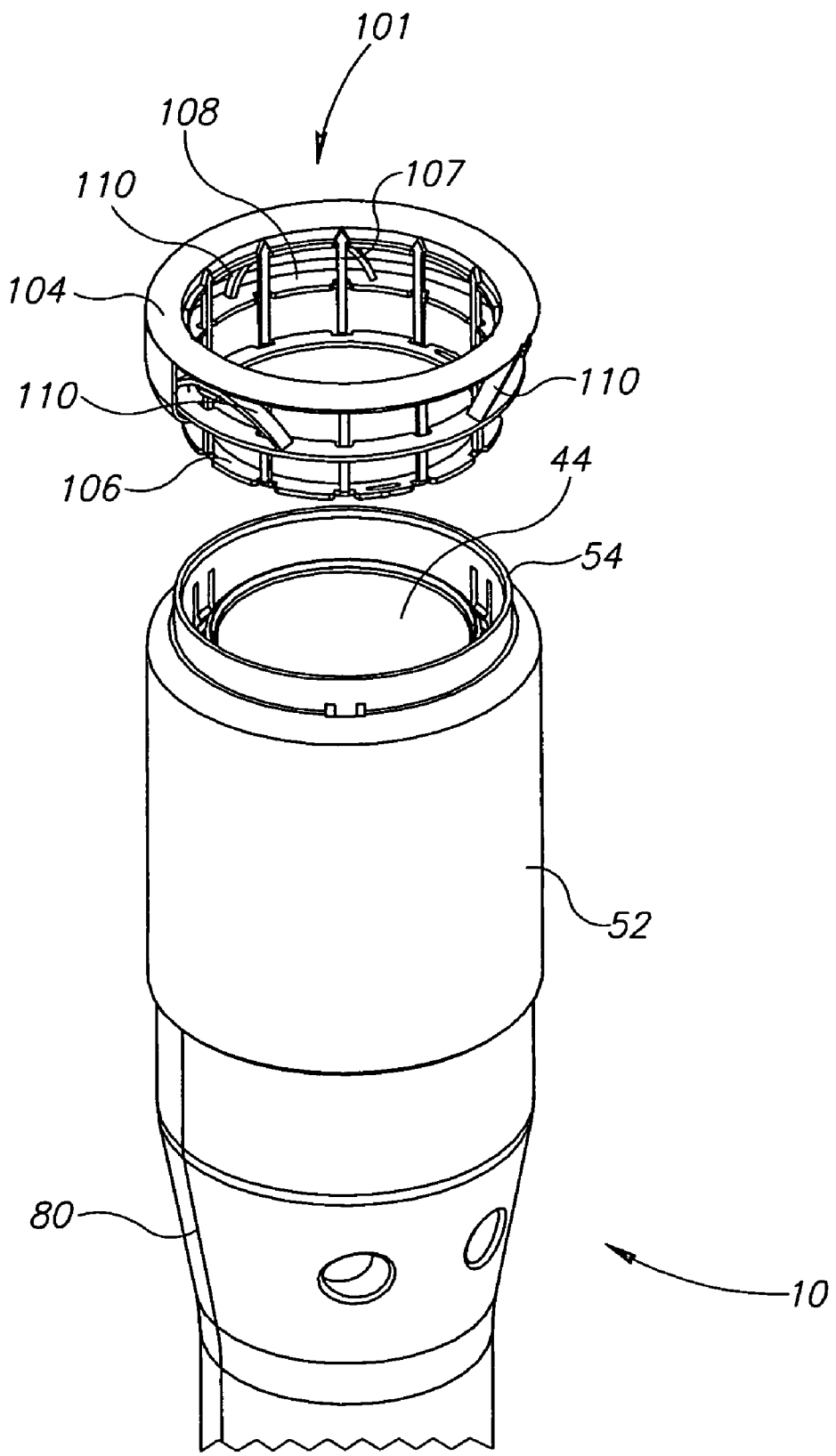
FIGS. 8A and 8B show a CAR assembly constructed according to the present invention being brought for positioning in a CAR applicator also constructed according to an embodiment of the present invention.
Figure 8B:
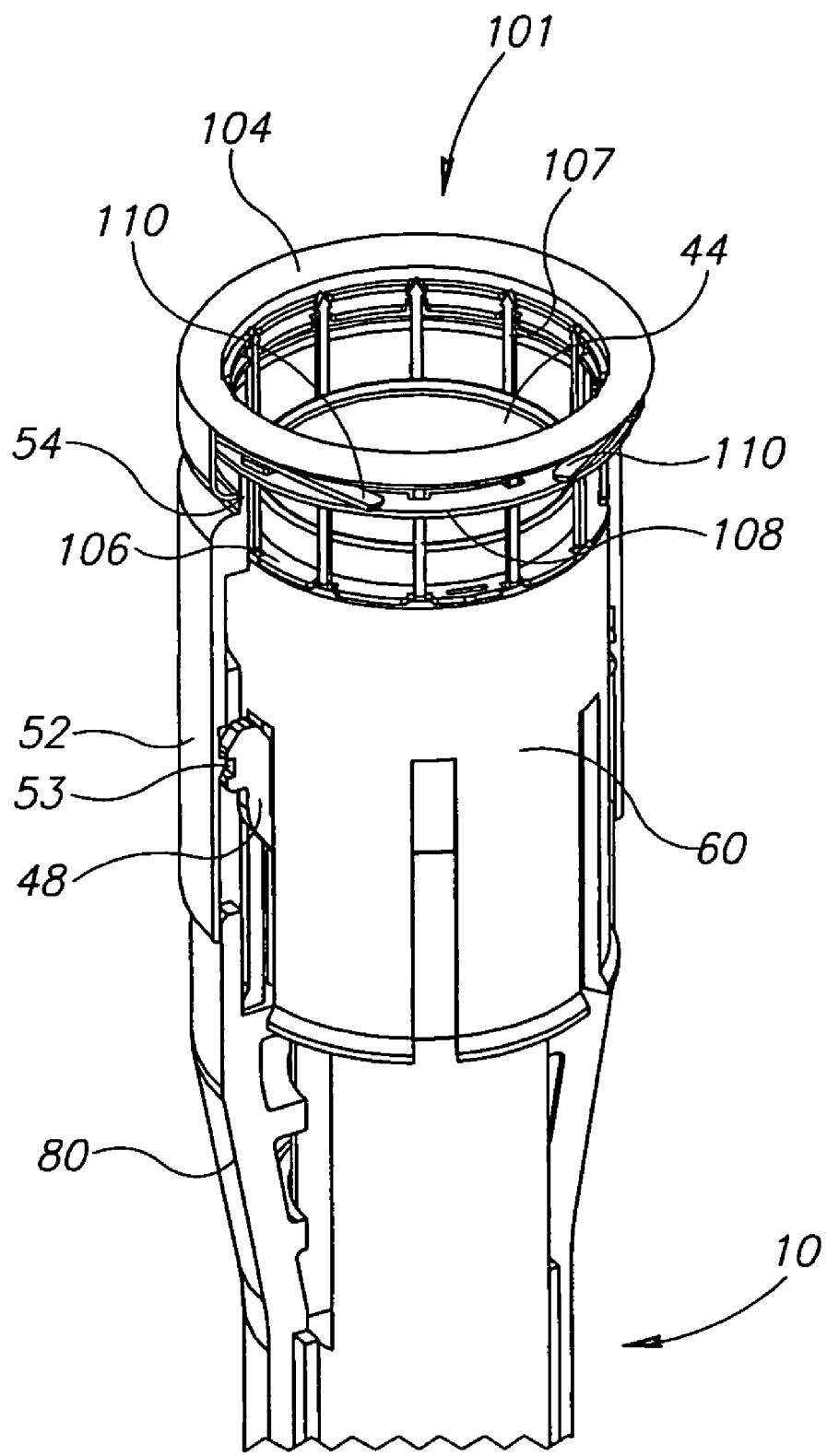

Reference is now made to FIGS. 8A and 8B which show two views of the second portion 101 of CAR assembly 100 in the process of being positioned and positioned on the distal end of CAR applicator 10, respectively. In FIGS. 8A and 8B, the rest of CAR applicator 10 is not shown. In FIG. 8A, CAR assembly 100 is shown with spring elements 110 in their non-compressed arched shape and with the shape-memory alloy from which they are formed in its non-stressed austenite phase. In FIG. 8B, spring elements 110 are compressed and flattened and the shape-memory alloy from which they are formed is in its stressed-induced martensite phase.

In FIGS. 8A and 8B, the second portion 101 of CAR assembly 100, as discussed previously, is shown to be comprised of a bottom ring 104, a CAR flange 108, a needle ring 106, a plurality of needles 107, here barbed needles, and a plurality of spring elements 110 formed of a shape-memory alloy. While somewhat obscured in FIG. 8B, there are in fact three spring elements located on CAR flange 108. This is intended to be an exemplary but non-limiting, number. In some instances there may even be a single spring element. Each spring element in FIGS. 8A and 8B is located an equidistance from its nearest neighbors on substantially circular CAR flange 108. Such an equidistant configuration is not intended to limit the use of other configurations and spacings.

The distal end of CAR applicator 10 includes a blade element 44, load lip 54, a ring support 52, applicator housing 80 and a step slider 60. Load lip 54 functions as a stress applier to spring elements 110 when loading the second portion 101 of CAR assembly 100 onto the distal portion of CAR applicator 10 as in FIG. 8B. When going from FIG. 8A to FIG. 8B, spring elements 110 have been flattened and the shape-memory alloy from which the spring elements are formed has been brought by load lip 54 to its stress-induced martensite state from its unstressed austenite state. The function of the other parts in these Figures and their interrelationship will be discussed in greater detail below in conjunction with FIGS. 9A through 13B.

As can readily be seen in FIG. 7, the circumference of the needle ring 106 is smaller than that of CAR flange 108. Accordingly, while CAR flange 108 is aligned with load lip 54, needle ring 106 is positioned and held inside ring support 52. Needle ring 106 rests against step slider 60 to be discussed below in conjunction with FIGS. 9A-13B.

Figure 14:
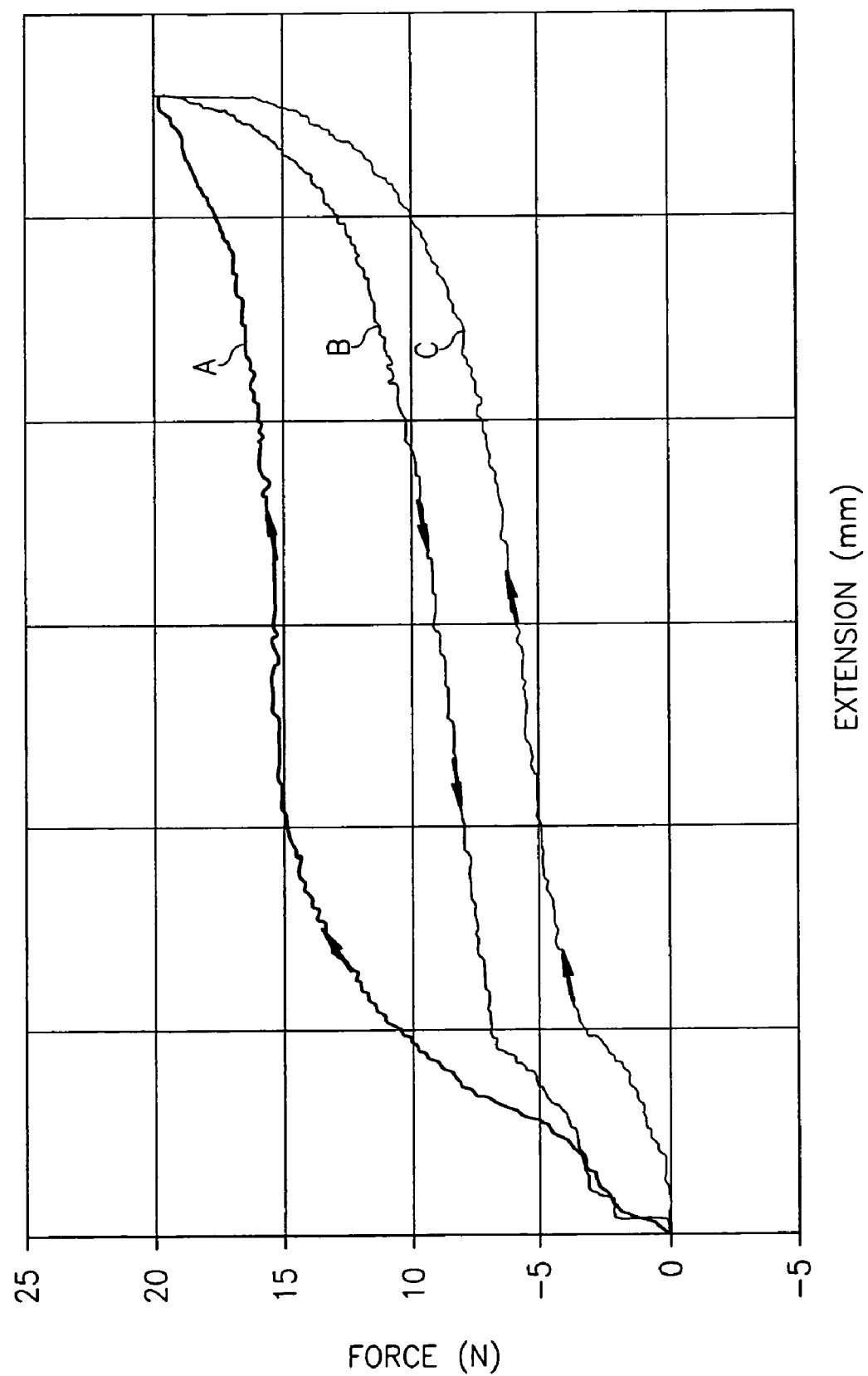
FIG. 14 shows typical shape-memory alloy stress-strain hysteresis loops produced by the shape-memory elements of a CAR assembly constructed according to an embodiment of the present invention.

In the Figures herein and in the accompanying discussion, a load lip 54 is described as providing the load that brings the alloy of spring elements 110 into its martensitic phase and the spring elements to their compressed flat configuration. It is readily understood that other load providing means, such as load teeth or load protrusions, positioned on the distal edge of ring support 52 at the distal end of the CAR applicator 10 may also be used. As will be described in greater detail in conjunction with FIG. 14 below, pre-loading, i.e. compressing, spring elements 110 allows direct use of only the bottom portion of the stress-strain hysteresis curve for the shape-memory alloy shown. Only when the CAR flange 108 is released is a relatively constant force, as reflected by the plateau-like region of curve B in FIG. 14, is applied on the tissue.

While we have described the flattening of spring elements 110 as being stress-induced, it should be understood that they may also be induced by a combination of stress and cooling as is typical with shape-memory alloys.

FIGS. 9A-13B, to which reference is now made, illustrate the operation of CAR assembly 100 in effecting anastomosis.

Figure 9A:
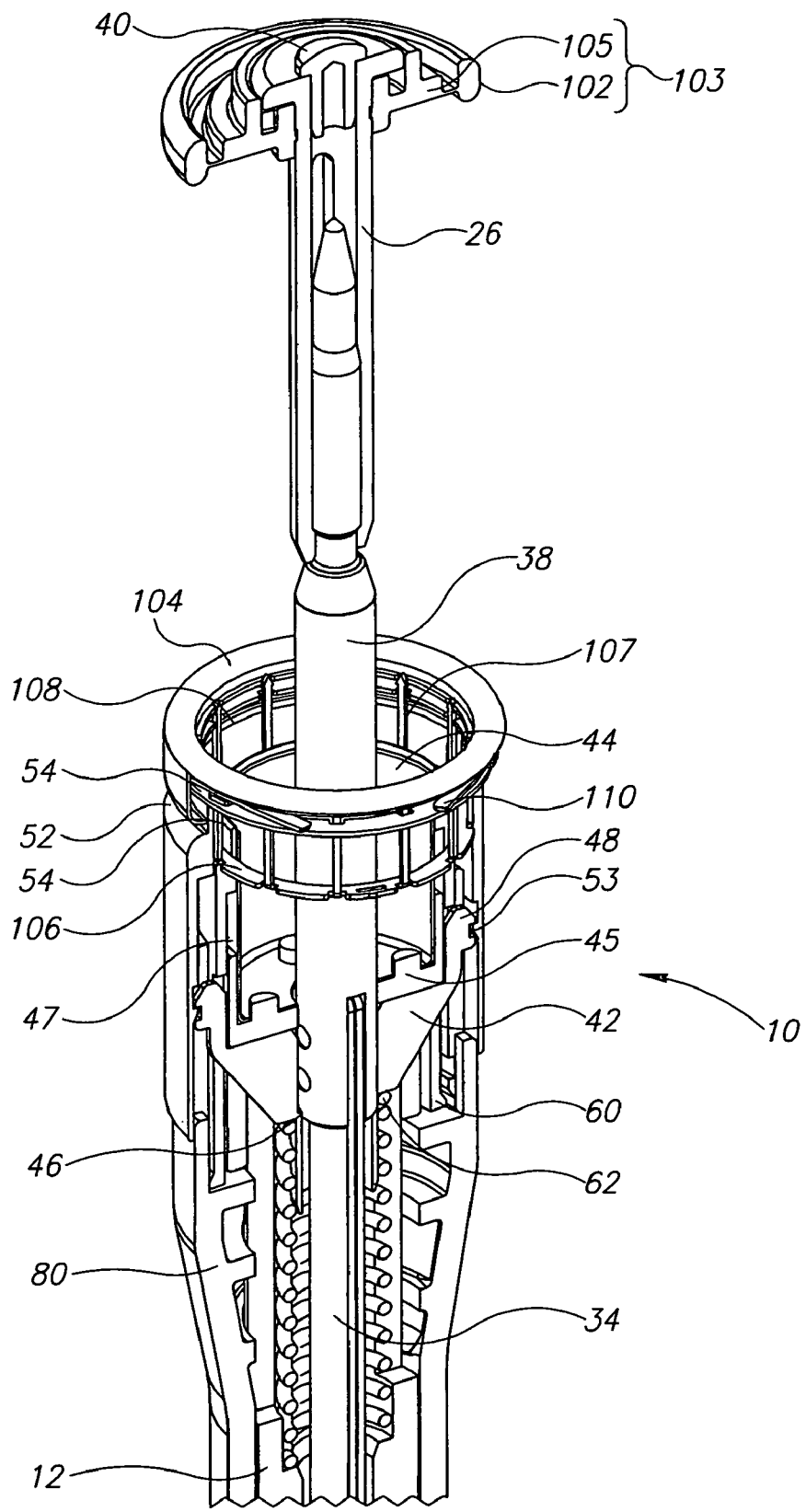
FIG. 9A shows a cut-away isometric view of the distal end of the CAR applicator and of the CAR assembly prior to applying the CAR assembly to the site requiring anastomosis.
Figure 9B:
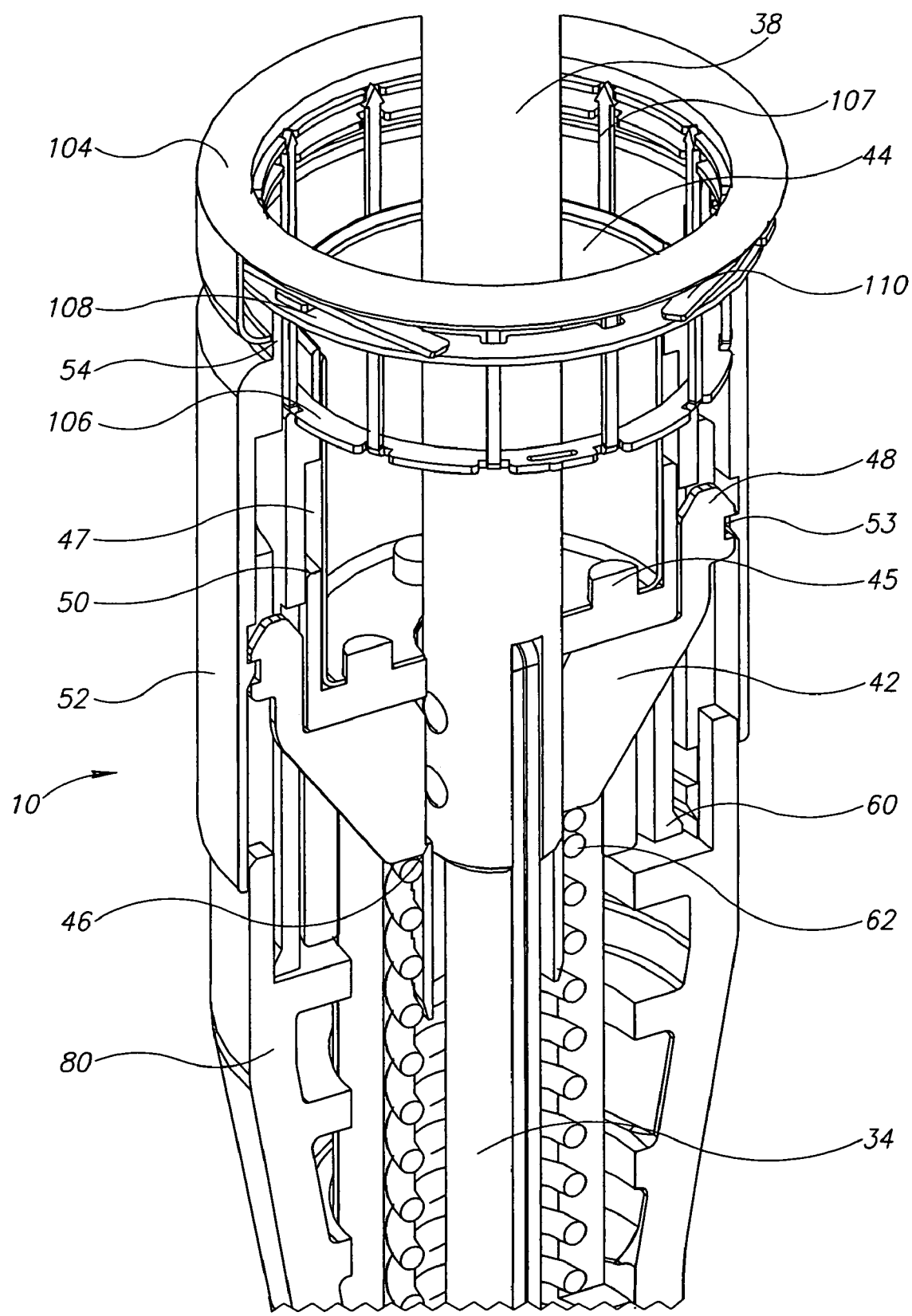
FIG. 9B is an enlarged view of the distal end of the CAR applicator and second portion of the CAR assembly shown in FIG. 9A.

FIGS. 9A and 9B show the initial step in the method of operation of CAR applicator 10 (best seen in FIGS. 2 and 3) and CAR assembly 100 (best seen in FIG. 7) after deploying the second portion 101 of CAR assembly 100 on the distal end of CAR applicator 10. The deploying procedure has been shown and discussed above in conjunction with FIGS. 8A and 8B. FIG. 9B is an expanded view of the lower portion of FIG. 9A. In both FIGS. 9A and 9B, shape memory alloy spring elements 110 have been compressed as previously discussed either by stress or cooling and stress.

Figure 9C:
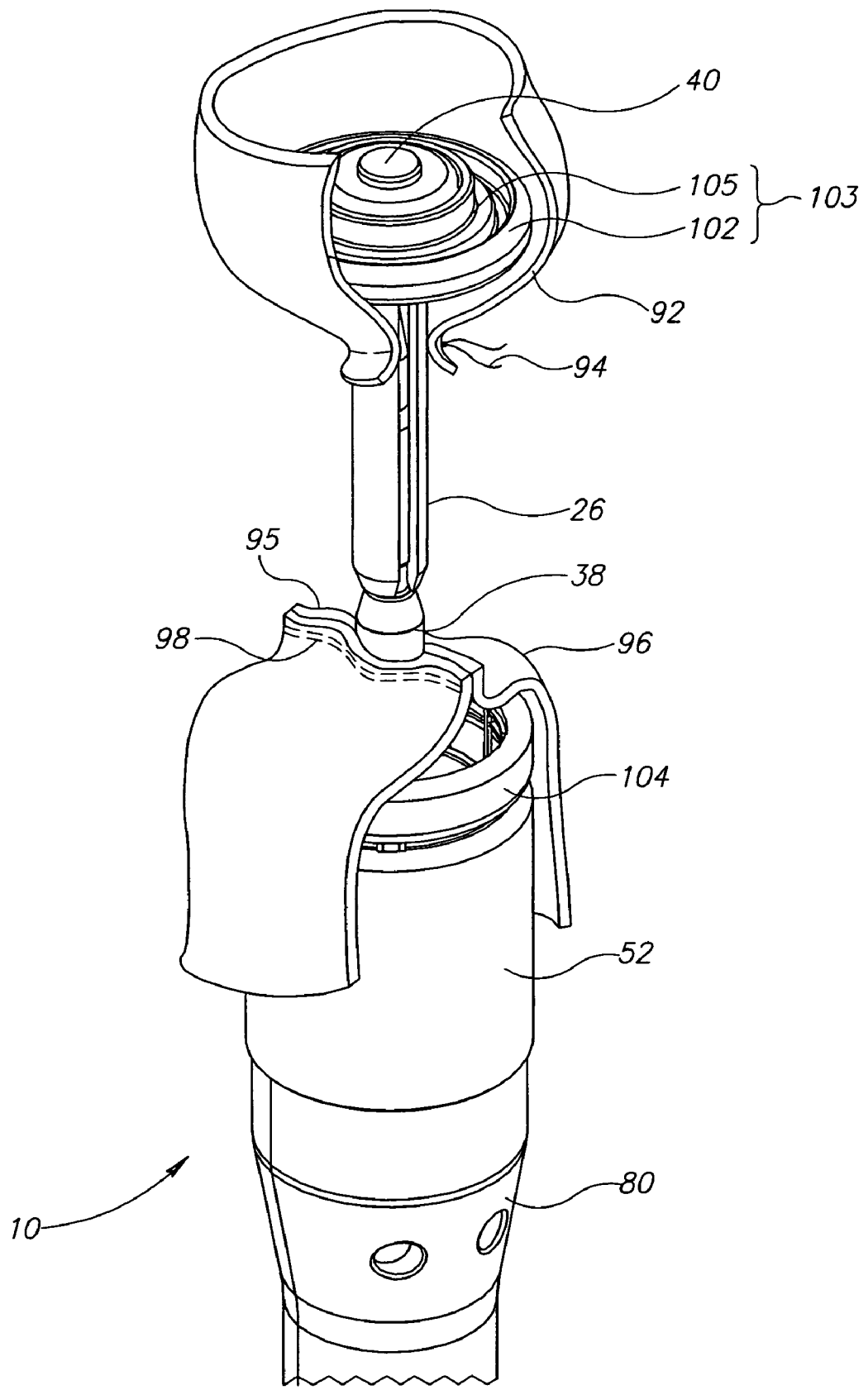
FIG. 9C shows the CAR assembly and CAR applicator of FIGS. 9A and 9B with tissue attached, the tissue intended to undergo anastomosis.

Turning control knob 24 (FIG. 1) on CAR applicator 10 (FIG. 1) extends trocar 38 past the distal end of applicator 10. Trocar 38 is joined by any of several means well-known to those skilled in the art to trocar connecting link 34 (best seen in FIG. 2). Anvil disk 103 is joined to trocar 38 by anvil rod 26. Rod 26 is tapered at its proximal end and extends into anvil disk 103 at its distal end. As shown in FIG. 9C, while trocar 38 is extended past the distal end of CAR assembly 10, a first cut end 92 of a cut body lumen is placed over anvil disk 103 and attached below disk 103 by a purse string suture 94. FIG. 9C is a full non-cut away view related to FIGS. 9A and 9B which includes the tissue sections to undergo anastomosis.

Prior to extending trocar 38 out of the distal end of CAR applicator 10, the applicator is inserted into the second part 96 of the severed lumen. This part has been sealed off at its end, herein called the second end 95, by any of several methods of suturing or stapling 98 known in the art. This sutured or stapled second end 95 is placed over the distal end of applicator 10, including over deployed bottom ring 104. When trocar 38 is advanced, it pierces this sutured or stapled second end 95 of the cut lumen. Pierced second end 95 effectively drapes over the distal end of applicator 10 and bottom ring 104 positioned thereon.

In addition to the elements previously discussed and numbered in previous Figures, additional elements are present at or near the distal end of CAR applicator 10 in FIGS. 9A and 9B. The distal end of CAR applicator 10 is encased in housing 80. As also noted previously, spring elements 110 at the second portion 101 of CAR assembly 100 are in their compressed/flattened configuration and the alloy from which the spring elements are formed are in their stressed-induced martensite state.

Figure 10A:
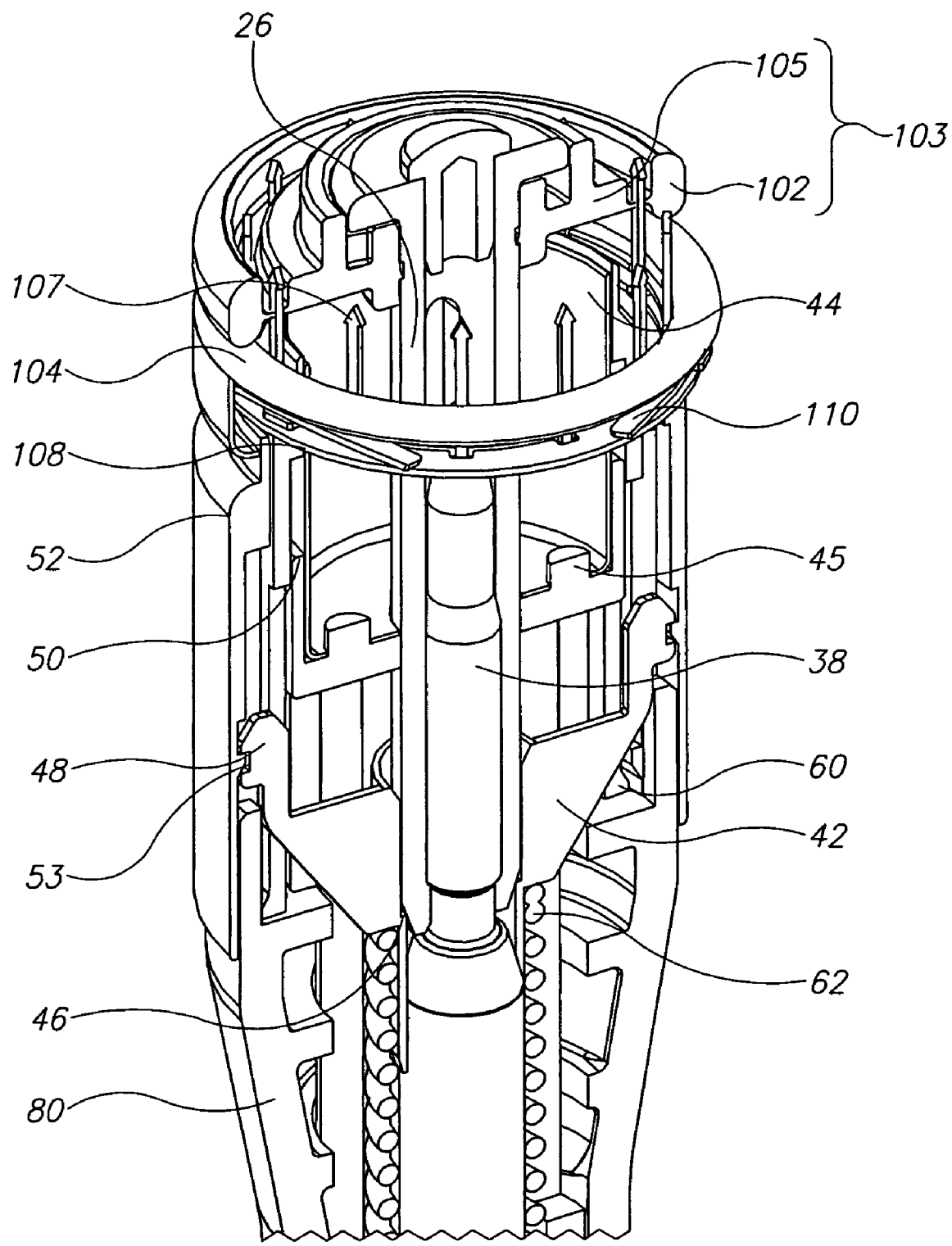
FIGS. 10A, 11A, 12 and 13A show the sequence of steps in the method of operation of the CAR assembly and CAR applicator shown in FIGS. 9A and 9B both constructed according to an embodiment of the present invention.

Shown in FIG. 9A is blade element 44 supported by blade holder 45 which is pushed by blade pusher 12. Anvil lock 42 (also shown in FIG. 3) lies above anvil lock spring 62 and has an anvil lock step 46 which locks anvil rod 26 when it is pulled back into housing 80 (FIG. 10A). Anvil lock 42 is also connected to ring support 52 by anvil lock arms 48 engaging with support ring flanges 53, forming an essentially single moving part therewith. Once anvil rod 26 engages anvil lock step 46 of anvil lock 42, rod 26 and lock 42 move downwards together in the direction of CAR applicator's 10 proximal end. Step slider 60, which rests on inside projections of housing 80, is separated from blade holder 45 by a gap 47 between step slider 60 and blade holder flange 50. The function of these parts will become evident and better illustrated in the course of the discussion which follows. The parts positioned at or near the distal end of CAR applicator 10 may be made from any of many metals or plastics known to those skilled in the art.

In FIG. 10A, to which reference is now made, anvil disk 103 has been brought close to bottom ring 104. The purse string attached tissue 92, attached to and surrounding anvil disk 103, and the stapled tissue 96, positioned over bottom ring 104 and the distal end of CAR applicator 10, are pierced by needles 107 of needle ring 106 as anvil disk 103 is brought towards bottom ring 104. Needles 107 enter and, as shown, pass through plastic anvil disk 103.

Moving anvil disk 103 to which the purse string attached tissue 92 has been affixed is effected by turning control knob 24 (FIG. 1). Knob 24 is in mechanical communication with trocar 38 inter alia by trocar connecting link 34, as has been discussed above in conjunction with FIG. 2. When moving from FIG. 9A to FIG. 10A, anvil disk 103, anvil rod 26 and trocar 38 are seen as being withdrawn toward and into housing 80, respectively.

In FIG. 10A, anvil rod 26 has engaged with anvil lock 42 at anvil lock step 46. Anvil rod 26, by engaging with anvil lock 42 pulls anvil lock 42 down as rod 26 is being retracted. This compresses anvil lock spring 62. Since anvil lock arms 48 engage with ring support flanges 53 on the internal side of ring support 52, support 52 also moves down. Bottom ring 104 moves downward along with ring support 52. As ring support 52 moves down it exposes needles 107 and releases its grip from needle ring 106 that holds bottom ring 104 in place. By piercing anvil disk 103, needles 107 help keep a constant gap between anvil ring 102 and bottom ring 104.

Figure 10B:
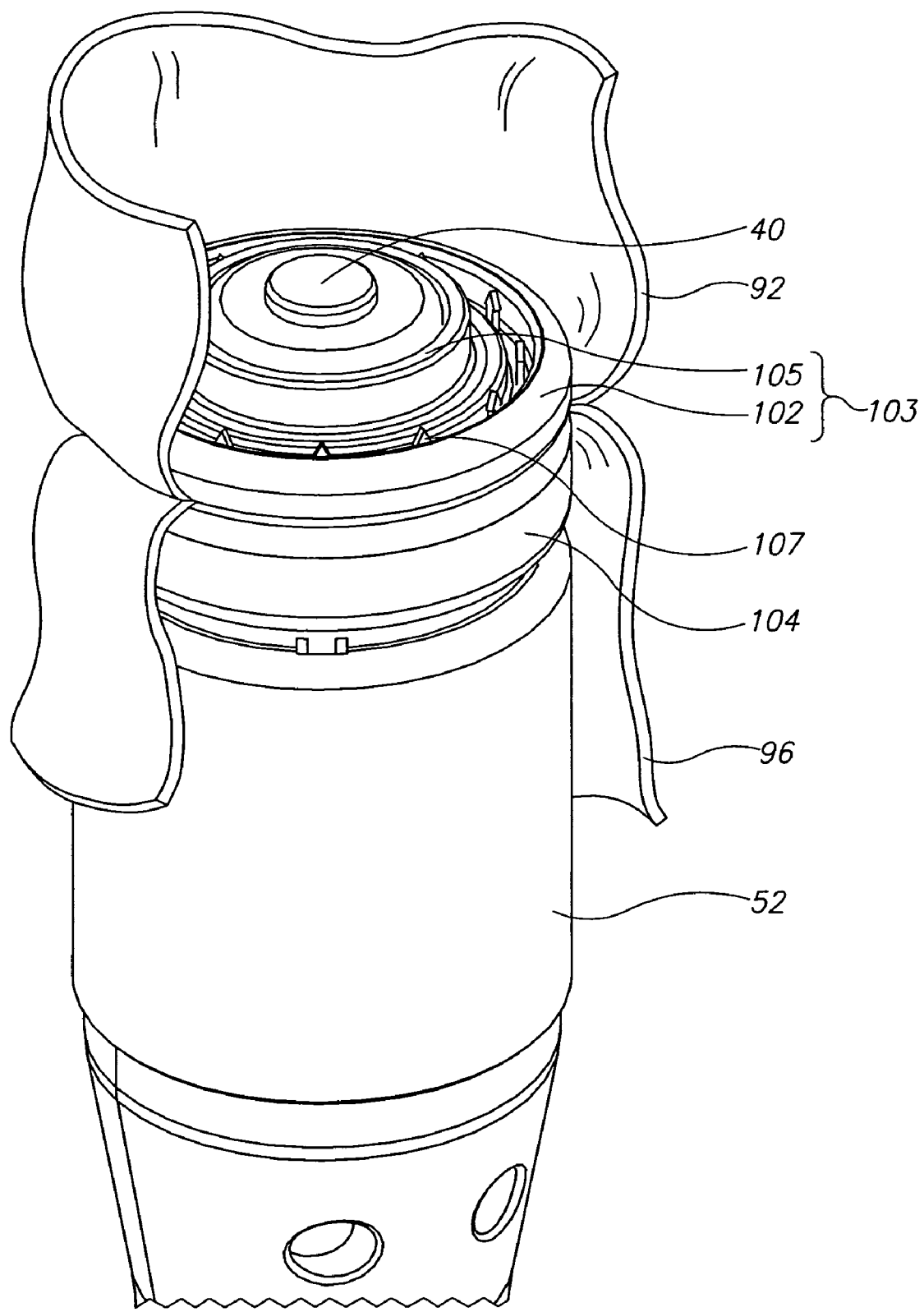
FIGS. 10B, 11B, and 13B show the position of the tissue to undergo anastomosis at the stages of operation shown in FIGS. 10A, 11A and 13A, respectively.

FIG. 10B shows a view of CAR assembly 100 and the distal end of CAR applicator 10 together with a cut-away view of the tissue to undergo anastomosis. FIG. 10B is presented at the same stage of operation as is shown in FIG. 10A. The purse string attached tissue 92 and the sutured or stapled tissue 96 are shown as being held between anvil ring 102 and bottom ring 104. The purse string 94 and suture/staples 98, shown in FIG. 9C, are obscured in FIG. 10B by bottom ring 104 and anvil ring 102.

Figure 11A:
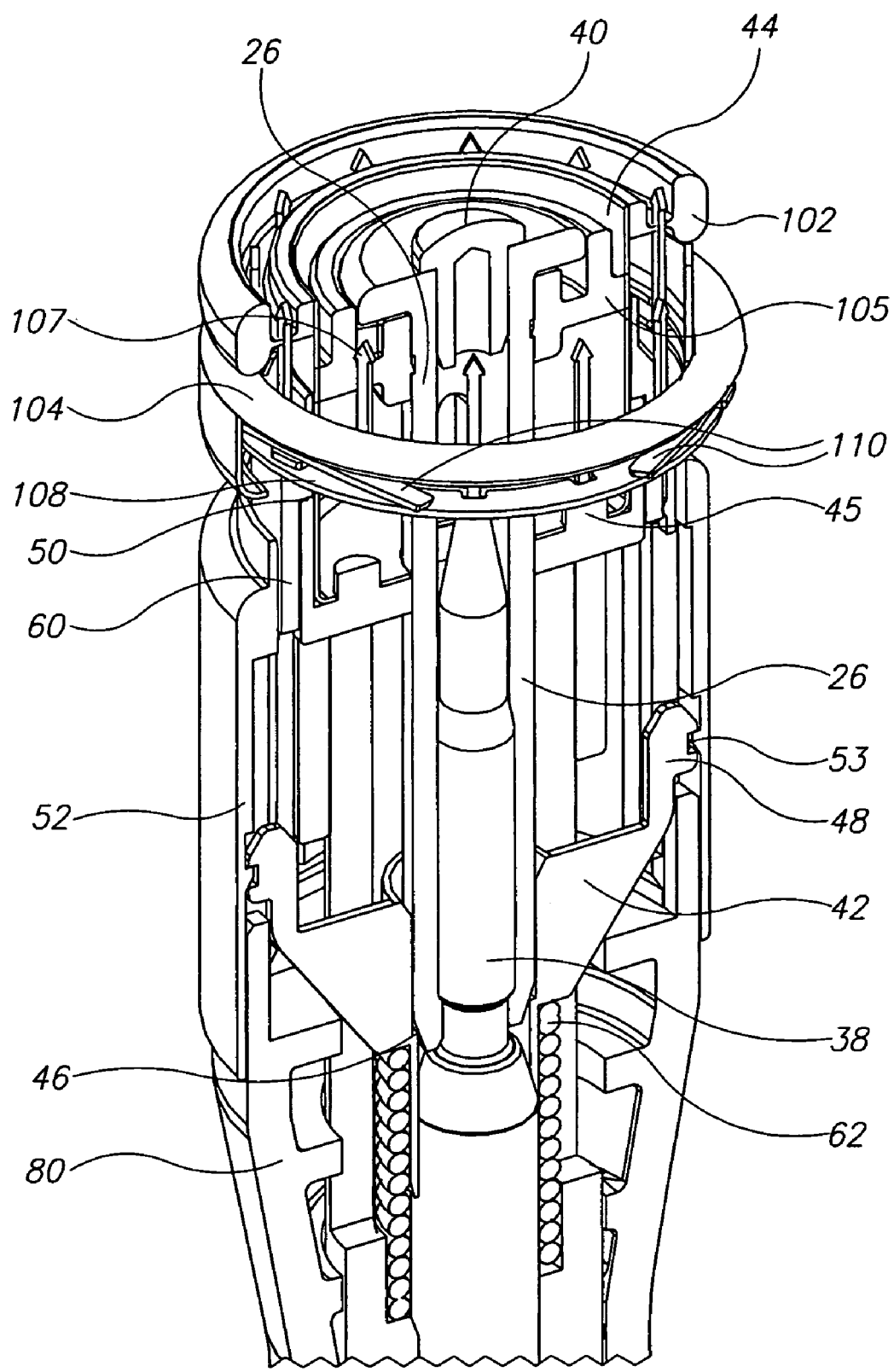

In FIG. 11A to which reference is now made, step slider 60 moves or "steps" up and gap 47 (best seen in FIGS. 9A and 9B) closes. Closure of this gap is effected when blade holder flange 50 engages with step slider 60. As blade element 44 moves up, it cuts both the purse string tied tissue 92 attached to anvil disk 103 and the tissue 96 draped over bottom ring 104. Additionally, plastic anvil disk 103 is cut into two concentric parts, an anvil ring inner core 105 which remains attached to anvil rod 26 and a free outer anvil ring 102. The latter remains detached from anvil rod 26 and is held in place by needles 107. Needle ring 106 is substantially stationary until anvil disk 103 is cut after which needle ring 106 is released from ring support 52.

When needles 107 penetrate anvil ring 102 they connect CAR bottom part 101 and anvil disk 103. At the same time needle ring 106 is released from ring support 52 so that the whole CAR assembly 100 is held only by anvil rod 26. Once anvil disk 103 is cut, CAR assembly 100 is actually held by blade element 44.

Figure 11B:
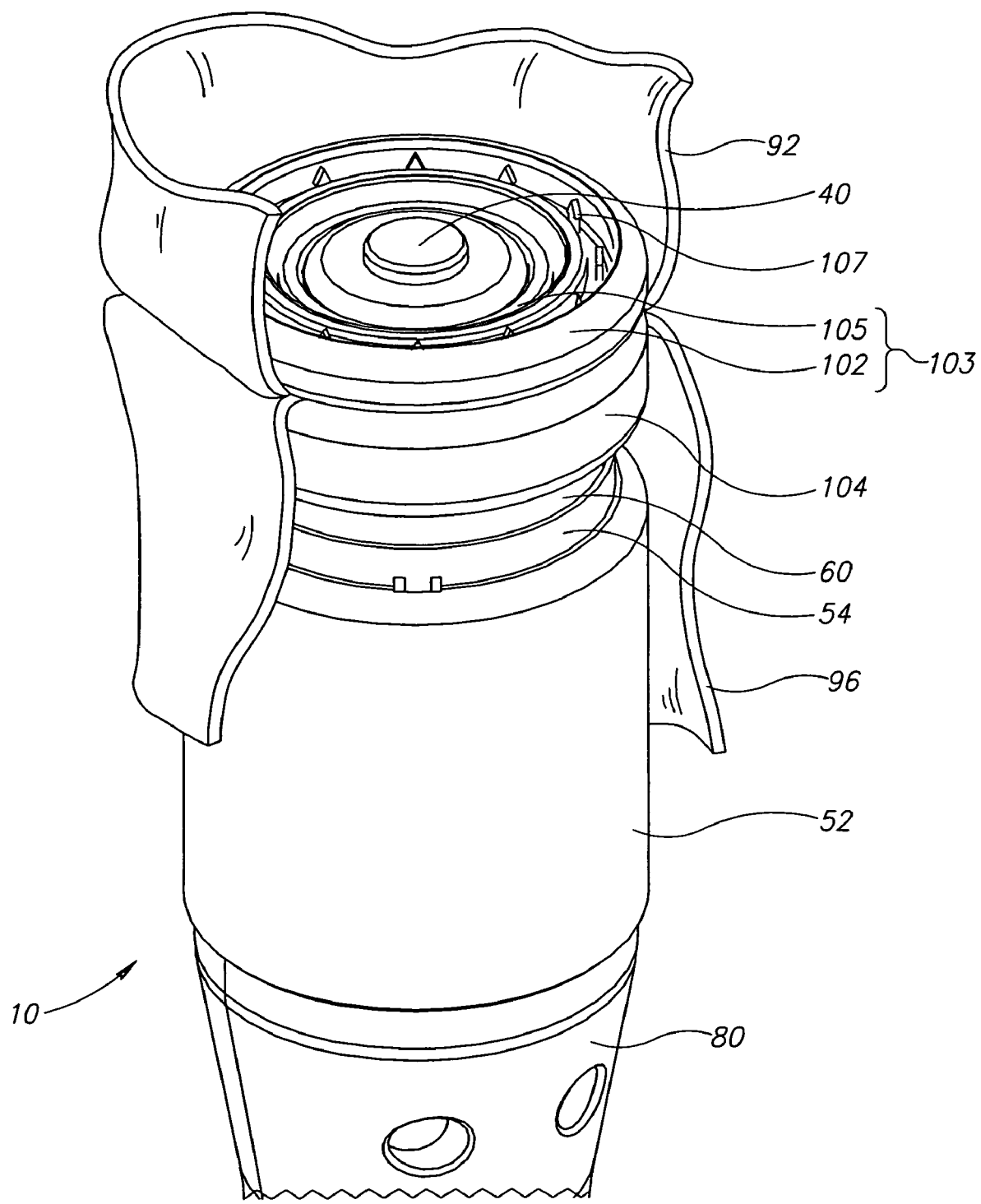

FIG. 11B shows a view of CAR assembly 100 and CAR applicator 10 together with a cut-away view of the tissue to undergo anastomosis. FIG. 11B is presented at the same stage of operation as is shown in FIG. 11A. FIG. 11B is very similar to FIG. 10B but the view of FIG. 11B shows the beginning of the separation of bottom ring 104 from the distal end of CAR applicator 10.

Figure 12:
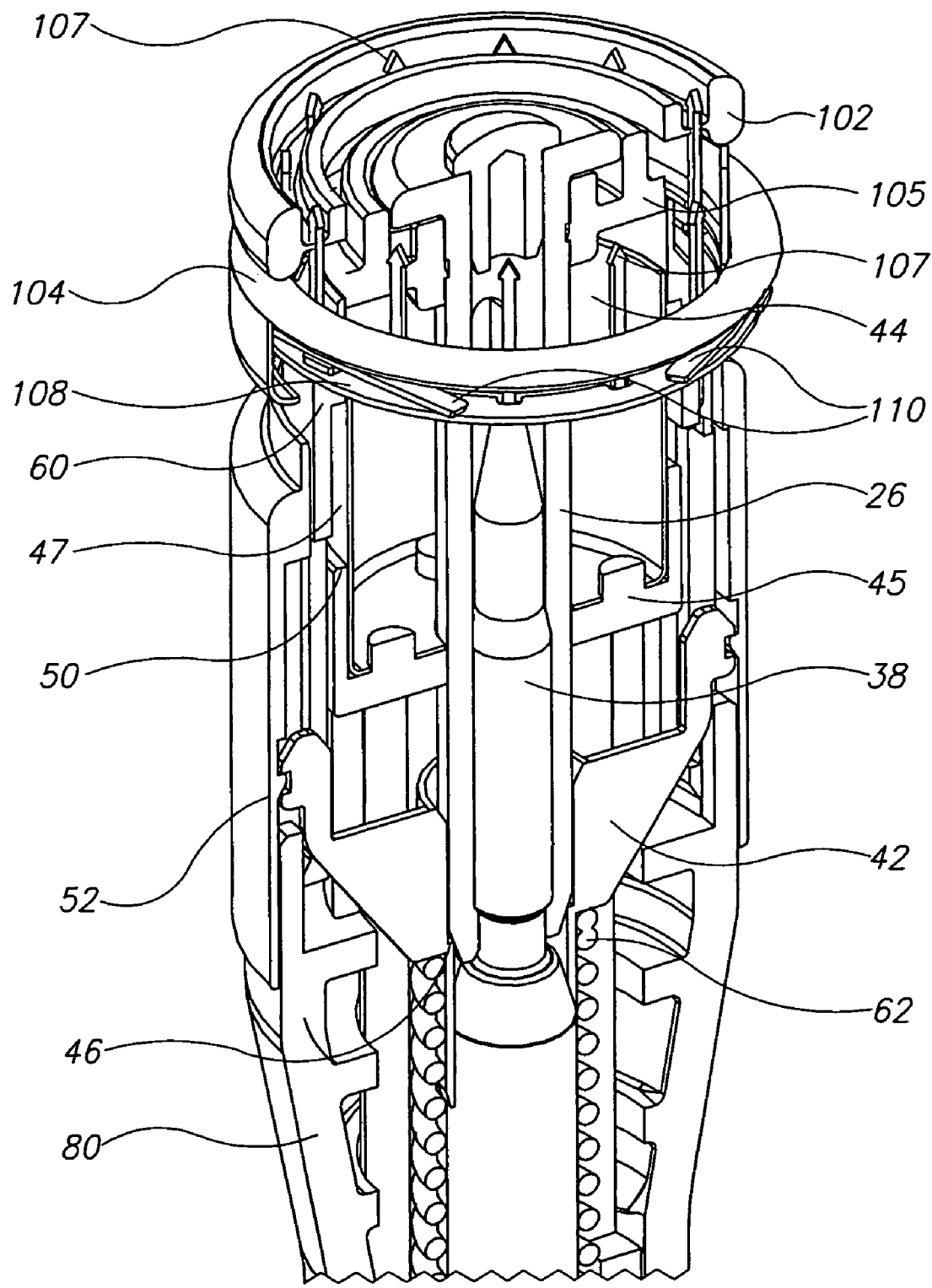

In FIG. 12, with the cutting operation completed, blade element 44 and blade holder 45 are pulled back by blade pusher 12 with which, as discussed in conjunction with FIG. 3 above, they are in mechanical connection. These parts are retracted by releasing lever 20 (FIG. 1). Meanwhile, bottom ring 104 of CAR assembly 100 detaches completely from step slider 60 allowing blade element 44 to release from anvil ring 102. When blade element 44 is pulled back, step slider 60 stops CAR assembly 100 and frees its bottom portion 101 from blade element 44. CAR assembly 100 is thus completely free from the distal end of CAR applicator 10.

Figure 13A:
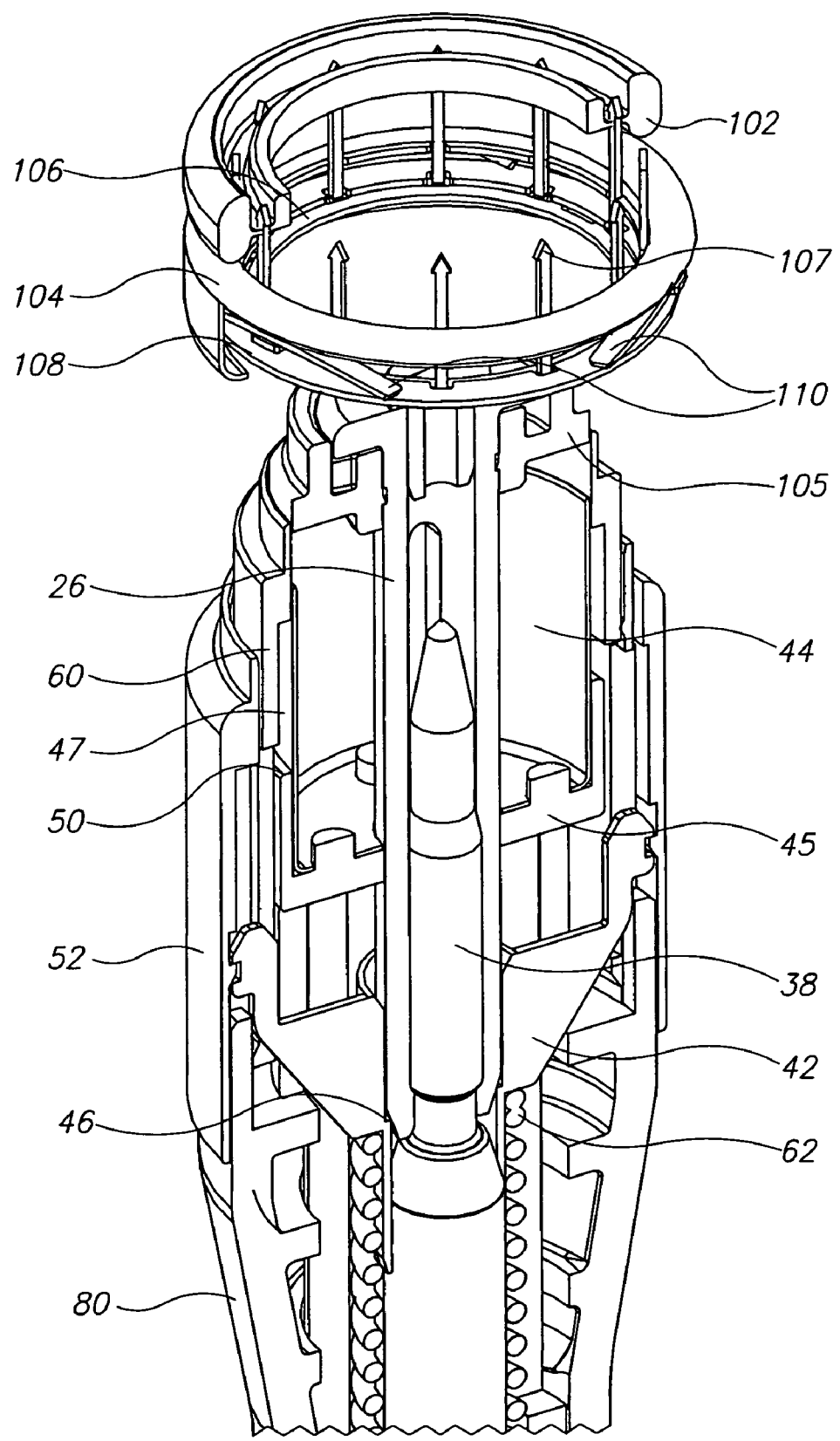

FIG. 13A, to which reference is now made, shows anvil and bottom rings 102 and 104, respectively, completely disengaged from CAR applicator 10. Still attached to anvil rod 26 is the inner circular core 105 cut from anvil disk 103 in FIG. 11A. In FIG. 13A, spring elements 110 begin to arch and abandon their flattened shape as they are no longer compressed by load lip 54. The arching spring elements 110, in force contact with bottom ring 104, exert a relatively constant force, as reflected by the plateau-like region of curve B in FIG. 14, that compresses the tissue sections held between disengaged bottom ring 104 and anvil ring 102.

Figure 13B:
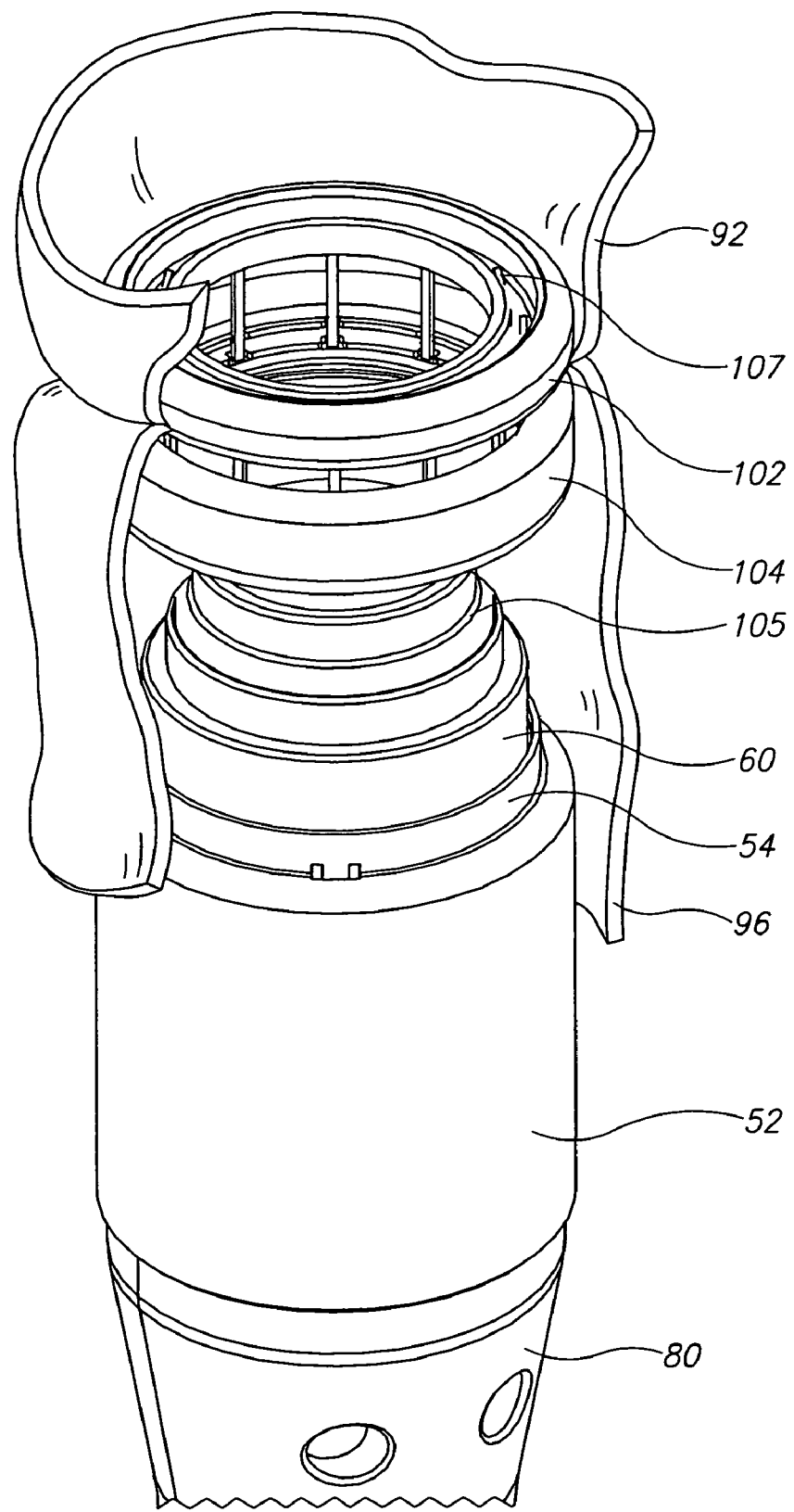

CAR applicator 10, anvil ring inner core 105, and anvil rod 26 are pulled away from the anastomosis site leaving the tissue as shown in FIG. 13B held between anvil ring 102 and bottom ring 104 to undergo anastomosis. After anastomosis, CAR assembly 100 is expelled from the body. In the case of anastomosis of the bowel, expulsion is through the anus.

While obscured in FIG. 13B, there are two donut shape pieces of cut tissue attached to retracted anvil rod 26. In FIG. 13B, anvil rod 26 and the attached donut-shaped pieces of tissue are inside blade 44 and therefore not visible.

It should be noted that in FIGS. 11A, 12A and 13A barbed needles are still inserted into anvil ring 102. The distance between anvil ring 102 and bottom ring 104 gradually closes as spring elements 110 arch. The compressive force on the tissue intended to effect anastomosis is generated by shape-memory alloy spring elements 110 acting on rings 102 and 104. As discussed further below this compressive force is a relatively constant compressive force as reflected by the plateau-like region in curve B of FIG. 14.

In FIG. 14, to which reference is now made, stress-strain (force-extension) hysteresis loops for a shape-memory (SM) alloy, here nitinol, are shown. As noted above, the spring elements 110 of the CAR assembly of the present invention are constructed of a shape-memory alloy, typically but without intending to be limiting, nitinol. They make use of the plateau region in curve B of the hysteresis loops shown. Curve B represents the removal of the shape-changing stress form spring elements 110. The plateau region in curve B indicates that a relatively constant force is exerted on the tissue for which anastomosis is being effected over a defined extension range.

The present invention has been described above as using stress-induced shape changes in spring elements 110. The hysteresis loop for such a situation is represented by curves A-B. The present invention also contemplates using shape changes induced by cooling and stress. A hysteresis loop, shown as curves C-B and having a similar plateau region in curve B reflects the situation when such conditions are employed. Arrows on the hysteresis loops of FIG. 14 show the direction in which the stress is applied and removed under each method of martensitic transformation.

It will be appreciated by persons skilled in the art, that in general, an apparatus employing a spring, spring elements 110 in the present invention, constructed of a shape memory (SM) alloy may be used in one of two ways. The alloy may be deformed at room temperature in its austenite state thus transforming it into its martensite state, often known as stress-induced martensite (SIM) (curve A). This employs the alloy's superelastic behavior. While in its SIM state, the spring's SM alloy is restrained in its deformed shape by a restraining means. After positioning the apparatus in the body and increasing the spring element's temperature to body temperature and removing the restraining means, the alloy returns to its austenite state and the spring to its original shape along a path represented by curve B. As the spring returns to its uncompressed configuration, it presses on the tissue with a relatively constant force, as reflected by the plateau-like region of curve B in FIG. 14, to bring about anastomosis.

In the second way of using a spring constructed from a shape memory (SM) alloy, the superelastic plasticity behavior of the alloy is employed. The alloy of the spring is first cooled transforming the alloy, at least partially, into its martensite state (curve C). The alloy is then deformed, i.e. the spring is then loaded, and retained using a special restraining means in its deformed martensite state. This martensite state is often referred to as the stress-retained martensite (SRM) state. The alloy/spring is then heated to body temperature. When the spring, in the present invention spring elements 110, is released from the restraining means at body temperature, the alloy returns to its austenite state, and the spring returns to its original uncompressed shape (curve B). As the spring returns to its original configuration, it presses on the tissue with a relatively constant force, as reflected by the plateau-like region of curve B in FIG. 14, to bring about anastomosis.

It should be noted that in both cases, the return to the austenite uncompressed, unloaded state from the compressed, loaded martensite state is along the same path, curve B. In both cases, the same relatively constant force, represented by the plateau region of curve B, is recovered.

FIG. 14 shows that a constant force (plateau region curve B) is being used in the present invention to bring about anastomosis. In prior art, on the other hand, any spring element used is constructed of regular, non-shape memory materials. Therefore, the force applied by these spring elements is in direct relation to displacement i.e. Hooke's law. Additionally, the maximum reversible strain of spring elements made from regular materials is on the order of about 0.3%. In view of the direct relationship to displacement in regular spring materials, the compressive force to effect anastomosis is a function of tissue thickness. Additionally, in view of the small reversible strain, a large "height", that is distance between the first and second portions of the CAR assembly, is required to provide the necessary compressive force.

As noted, the first factor, in effect, makes the anastomosis process in prior art devices a function of tissue thickness. However, in order to get good anastomosis with a good strong seal at the join, approximately the same force should be applied throughout the process, and the force should be essentially the same irrespective of tissue thickness. It should also be noted that too much force may lead to premature detachment of the CAR assembly, possibly even before healthy new scar tissue is formed. Too little force may result in the CAR assembly detaching only after a very long time. Alternatively, it may not effect ischemia. Spring elements formed from shape-memory alloys, as in the present invention, provide a relatively constant force independent of tissue thickness, as reflected by the plateau-like region of curve B in FIG. 14.

As also noted, the second factor discussed above, that is the small reversible strain of regular spring materials, requires an increased "height" of the CAR assembly. This increase in size would inter alia impair the assembly's expulsion from the bowel after anastomosis has been completed.

The use of a shape memory alloy, typically nitinol, for forming a spring element, as in the present invention, allows for the use of a relatively thin nitinol leaf as a spring element. The leaf typically may be about 0.5 mm thick. When the leaf deforms, the CAR "height", the distance between the first and second portions of the CAR assembly, is relatively small. What is herein described as being a small leaf spring allows for the use of nitinol's large reversible deformation (~6%) as opposed to a regular material's small reversible deformation (~0.3%). With regular spring material similar deformations can not be achieved; a physically larger spring such as a spring coil must be used. This would lead to larger "heights" for the CAR assemblies and the concomitant difficulties discussed above.

It will be appreciated by persons skilled in the art that there is a direct relationship between the size and thickness of the CAR assembly 100 and applicator 10 used in the surgical procedure disclosed above and the size, shape and type of organ to be treated. A CAR assembly 100 of a particular size is selected so as to achieve an aperture of a requisite size as appropriate to the situation and the hollow organ to be subjected to anastomosis. Clearly, a smaller size is appropriate for use in the upper bowel and a larger size in the lower bowel.

It should also be understood that the present invention also contemplates a case where spring elements 110 may be deployed in their unloaded, uncompressed, here arched, configuration. In such a configuration, the alloy from which the spring elements are formed is initially in its austenite state. After the second portion 101 of CAR assembly 100 is deployed in its unloaded austenite state on the distal end of CAR applicator 10, a load can be applied to CAR flange 108. Such a load can be applied by a load lip, load teeth or load protrusions. After bringing spring elements 110 to their loaded martensite state, anvil disk 103 of the CAR assembly 100 is brought towards the second portion 101 of CAR assembly 100 with tissue to be anastomosized held therebetween. When the tissue is held sufficiently securely by anvil disk 103 and second portion 101, spring elements 110 are unloaded and they begin to arch causing bottom ring 104 of CAR assembly 100 to compress the tissue held against anvil disk 103 and anastomosis can occur. In this embodiment, as in prior embodiments, spring elements 110 may be positioned on CAR flange 108 and in contact with bottom ring 104. Alternatively, when no CAR flange is present spring elements 110 may be positioned on needle ring 106 so that it is in contact with bottom ring 104.

It will be appreciated by persons skilled in the art that the present invention is not limited by the drawings and description hereinabove presented. Rather, the invention is defined solely by the claims that follow.

What is claimed is:

1. A compression anastomosis ring (CAR) assembly which comprises:
    a first portion which comprises:
        an anvil ring; and
    a second portion which comprises:
        a bottom ring positioned substantially parallel to and spaced apart from said anvil ring, said anvil ring and said bottom ring being adapted to be brought together in the presence of a closure force applied thereacross:
        at least one ring element, where one of said at least one ring elements is a needle ring positioned on a side of said bottom ring distal from said anvil ring, said needle ring having a plurality of needles extending generally transversely therefrom toward said first portion; and
        at least one spring element which provides a restorative force formed at least partially of a shape-memory alloy, said spring element positioned on one of said at least one ring elements and being in compressive force transmissive contact with said bottom ring, and
    wherein when said compression anastomosis ring (CAR) assembly is positioned so as to hold between said anvil ring and said bottom ring tissue portions to be compressed and joined by anastomosis, said needle ring is operative, in response to the closure force to drive said plurality of needles through the tissue portions to be compressed and to anchor said plurality of needles in said anvil ring, and
    wherein when said anvil ring and said bottom ring are brought together in the presence of the closure force holding the tissue portions therebetween, and when said anvil ring is anchored by said plurality of needles, the restorative force provided by said at least one spring element is operative on said bottom ring to compress said tissue portions thereby effecting anastomosis.

2. A compression anastomosis ring (CAR) assembly according to claim 1 wherein said at least one spring element is positioned on said needle ring so as to be in compressive force transmissive contact with said bottom ring.

3. A compression anastomosis ring (CAR) assembly according to claim 1 wherein said at least one ring element is at least two ring elements, where one of said at least two ring elements is said needle ring and another of said at least two ring elements is a compression anastomosis flange (CAF) formed as a ring and positioned inside said bottom ring.

4. A compression anastomosis ring (CAR) assembly according to claim 3 wherein said CAF is positioned between said needle ring and said bottom ring, and said at least one spring element is positioned on said compression anastomosis flange (CAF) so as to be in compressive force transmissive contact with said bottom ring.

5. An assembly according to claim 1 wherein said anvil ring is made from a polymeric material and is integrally formed together with an inner core also fabricated from a polymeric material.

6. An assembly according to claim 5 wherein said needles are operable to penetrate and pass through said anvil ring in response to a predetermined force applied to said needle ring.

7. An assembly according to claim 5 wherein said anvil ring includes a plurality of holes in apposition to and in registration with said plurality of needles allowing entry of said needles and passage through said anvil ring in response to a predetermined force applied to said needle ring.

8. An assembly as in claim 1 wherein said at least one spring element is brought to its compressed configuration and the alloy from which it is formed is brought to its martensitic state by positioning said CAR assembly on a CAR applicator before bringing the tissue to be joined by anastomosis between said anvil ring and said bottom ring.

9. An assembly as in claim 8 wherein said at least one spring element is brought to its compressed configuration and the alloy from which it is formed to its martensitic state by applying thereto a compressive stress.

10. An assembly as in claim 8 wherein said at least one spring element is brought to its compressed configuration and the alloy from which it is formed is brought to its martensitic state by cooling and then applying thereto a compressive stress.

11. An endoluminal anastomosis apparatus for joining preselected organ wall portions of a hollow organ, said apparatus including:
a) a compressive anastomosis ring (CAR) assembly which comprises:
    a first portion which comprises:
    an anvil ring; and
    a second portion which comprises:
    a bottom ring positioned substantially parallel to and spaced apart from said anvil ring, said anvil ring and said bottom ring being adapted to be brought together in the presence of a closure force applied thereacross:
    at least one ring element, where one of said at least one ring elements is a needle ring positioned on a side of said bottom ring distal from said anvil ring, said needle ring having a plurality of needles extending generally transversely therefrom toward said first portion; and
    at least one spring element which provides a restorative force formed at least partially of a shape-memory alloy, said spring element positioned on one of said at least one ring elements and being in compressive force transmissive contact with said bottom ring, and
    wherein when said compression anastomosis ring (CAR) assembly is positioned so as to hold between said anvil ring and said bottom ring tissue portions to be compressed and joined by anastomosis, said needle ring is operative, in response to the closure force to drive said plurality of needles through the tissue portions to be compressed and to anchor said plurality of needles in said anvil ring, and
    wherein when said anvil ring and said bottom ring are brought together in the presence of the closure force holding the tissue portions therebetween and when said anvil ring is anchored by said plurality of needles, the restorative force provided by said at least one spring element is operative on said bottom ring to compress said tissue portions thereby effecting anastomosis; and
b) an endoluminal CAR applicator having a proximal end and a distal end, said applicator comprising:
    i) attachment means including an anvil rod extendable from said applicator, adapted to attach and hold said first portion thereto and operable to move said attached first portion toward said second portion of said CAR assembly;
    ii) deployment means positioned on said distal end of said applicator and operable to deploy said second portion of said CAR assembly positioned thereon so that said at least one spring element may be compressed and so that said plurality of needles may be brought to a position where they pierce said anvil ring and the tissue portions to be joined by anastomosis;
    iii) a blade element positioned in spaced relationship with said deployment means, said blade element operable to cut through said first portion and the tissue sections held between said anvil ring and said bottom ring of said assembly, subsequent to operation of said attachment means so as to bring said anvil ring in proximity to said bottom ring ond operation of deployment means so as to deploy said second portion of said CAR assembly so that said plurality of needles may be brought to a position where they pierce said anvil ring and the tissue portions to be joined by anastomosis; and
    iv) at least one activator of said applicator, each activator operationally connected to at least one of said deployment means, said attachment means and said blade element for activating said attachment means, said deployment means and said blade element.

12. An apparatus according to claim 11 wherein said at least one spring element is positioned on said needle ring so as to be in compressive force transmissive contact with said bottom ring.

13. An apparatus according to claim 11 wherein said at least one ring element is at least two ring elements, where one of said at least two ring elements is said needle ring and another of said at least two ring elements is a compression anastomosis flange (CAF) formed as a ring and positioned inside said bottom ring.

14. An apparatus according to claim 13 wherein said CAF is positioned between said needle ring and said bottom ring, and said at least one spring element is positioned on said compression anastomosis flange (CAF) so as to be in compressive force transmissive contact with said bottom ring.

15. An apparatus according to claim 11 wherein said anvil ring is made from a polymeric material and is integrally formed together with an inner core also fabricated from the polymeric material.

16. An apparatus as in claim 15, wherein when said blade element cuts through said first portion of said CAR assembly, said anvil ring is severed from said inner core and detached from said attachment means, said anvil ring then being held to said bottom portion by said plurality of needles so that said anvil ring is in registration with said bottom ring serving as an anvil for said bottom ring when said at least one spring element presses on said bottom ring compressing the tissue portions held therebetween.

17. An apparatus according to claim 11 wherein said deployment means further comprises a load means positioned in force transmissive contact with said deployment means so that when said at least one spring element is deployed, said load means exerts a load on said at least one spring element thereby bringing it to its compressed configuration and the alloy from which it is formed to its martensitic state.

18. An apparatus according to claim 17 wherein said at least one spring element is cooled before said load means exerts a load on, and compresses, said at least one spring element.

* * * * *